United States Patent
Padrick et al.

(10) Patent No.: US 9,307,904 B2
(45) Date of Patent: *Apr. 12, 2016

(54) OPTICAL ANGULAR MEASUREMENT SYSTEM FOR OPHTHALMIC APPLICATIONS AND METHOD FOR POSITIONING OF A TORIC INTRAOCULAR LENS WITH INCREASED ACCURACY

(71) Applicant: WaveTec Vision Systems, Inc., Aliso Viejo, CA (US)

(72) Inventors: Thomas D. Padrick, Seattle, WA (US); Jack T. Holladay, Bellaire, TX (US); Dan Bao Tran, Long Beach, CA (US); Aric K. Plumley, Huntington Beach, CA (US); Richard J. Michaels, Irvine, CA (US); Jeff Padgett, Long Beach, CA (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/046,748

(22) Filed: Oct. 4, 2013

(65) Prior Publication Data

US 2014/0132922 A1 May 15, 2014

Related U.S. Application Data

(63) Continuation of application No. 12/614,344, filed on Nov. 6, 2009, now Pat. No. 8,550,624.

(60) Provisional application No. 61/112,148, filed on Nov. 6, 2008, provisional application No. 61/166,660, filed on Apr. 3, 2009.

(51) Int. Cl.
*A61B 3/10* (2006.01)
*A61B 3/00* (2006.01)
(Continued)

(52) U.S. Cl.
CPC . *A61B 3/13* (2013.01); *A61B 3/152* (2013.01); *A61F 2/1613* (2013.01)

(58) Field of Classification Search
CPC .......... A61B 3/103; A61B 3/14; A61B 3/113; A61B 3/125; A61B 3/1225; A61B 3/107; A61B 3/1015
USPC ......... 351/200, 205–206, 209–211, 219, 221, 351/246–247
See application file for complete search history.

(56) References Cited

U.S. PATENT DOCUMENTS 4,125,320 A 11/1978 Rassow
4,172,662 A 10/1979 Vogel
(Continued)

FOREIGN PATENT DOCUMENTS

AU 2005234778 8/2011
CA 2515010 5/2013
(Continued)

OTHER PUBLICATIONS

International Search Report and Written Opinion for International Application No. PCT/US2009/063651 mailed Mar. 9, 2010.
(Continued)

*Primary Examiner* — Dawayne A Pinkney
(74) *Attorney, Agent, or Firm* — Baker Botts L.L.P.

(57) ABSTRACT

An ophthalmic system for use in performing angular measurements in relation to a patient's eye. The ophthalmic system can include an optical angular measurement device that can provide angular indicia by, for example, projecting an image of an angular measurement reticle onto a patient's eye or by superimposing an image of an angular measurement reticle onto an image of the patient's eye. The ophthalmic system can include an optical refractive power measurement device for providing desired angular orientations for ocular implants or for incisions. The ophthalmic system can be used, for example, to align a toric intraocular lens to a desired angular orientation.

38 Claims, 17 Drawing Sheets

(51) Int. Cl.
*A61B 3/13* (2006.01)
*A61B 3/15* (2006.01)
*A61F 2/16* (2006.01)

(56) References Cited

U.S. PATENT DOCUMENTS

| | | | |
|---|---|---|---|
| 4,173,398 A | 11/1979 | Okamoto et al. |
| 4,293,198 A | 10/1981 | Kohayakawa et al. |
| 4,353,625 A | 10/1982 | Nohda et al. |
| 4,372,655 A | 2/1983 | Matsumura et al. |
| 4,376,573 A | 3/1983 | Matsumura et al. |
| 4,390,255 A | 6/1983 | Nohda et al. |
| 4,421,391 A | 12/1983 | Matsumura et al. |
| 4,459,027 A | 7/1984 | Kafri et al. |
| 4,541,697 A | 9/1985 | Remijan |
| 4,640,596 A | 2/1987 | Humphrey |
| 4,650,301 A | 3/1987 | Humphrey |
| 4,669,835 A | 6/1987 | Humphrey |
| 4,692,003 A | 9/1987 | Adachi et al. |
| 4,710,193 A | 12/1987 | Volk |
| 4,721,379 A | 1/1988 | L'Esperance |
| 4,730,917 A | 3/1988 | Krueger |
| 4,911,711 A | 3/1990 | Telfair et al. |
| 4,964,715 A | 10/1990 | Richards |
| 4,984,883 A | 1/1991 | Winocur |
| 4,995,716 A | 2/1991 | Warnicki et al. |
| 5,080,477 A | 1/1992 | Adachi |
| 5,157,427 A | 10/1992 | Humphrey |
| 5,164,750 A | 11/1992 | Adachi |
| 5,206,672 A | 4/1993 | Rowe |
| 5,208,619 A | 5/1993 | Campbell |
| 5,223,863 A | 6/1993 | Heine |
| 5,252,999 A | 10/1993 | Sukigara |
| 5,258,791 A | 11/1993 | Penney et al. |
| 5,270,749 A | 12/1993 | Okamura |
| 5,282,852 A | 2/1994 | Capetan et al. |
| 5,294,971 A | 3/1994 | Braunecker et al. |
| 5,307,097 A | 4/1994 | Baker |
| 5,329,322 A | 7/1994 | Yancey |
| 5,374,193 A | 12/1994 | Trachtman |
| 5,450,143 A | 9/1995 | Rowe et al. |
| 5,455,645 A | 10/1995 | Berger et al. |
| 5,493,109 A | 2/1996 | Wei et al. |
| 5,576,780 A | 11/1996 | Yancey |
| 5,777,719 A | 7/1998 | Williams et al. |
| 5,796,463 A | 8/1998 | Bullimore |
| 5,800,533 A | 9/1998 | Eggleston et al. |
| 5,841,511 A * | 11/1998 | D'Souza et al. ............... 351/212 |
| 5,861,937 A | 1/1999 | Fujieda |
| 5,909,268 A | 6/1999 | Isogai et al. |
| 5,936,706 A | 8/1999 | Takagi |
| 5,949,521 A | 9/1999 | Williams et al. |
| 5,963,300 A | 10/1999 | Horwitz |
| 5,968,095 A | 10/1999 | Norrby |
| 5,994,687 A | 11/1999 | Chanteloup et al. |
| 6,002,484 A | 12/1999 | Rozema et al. |
| 6,004,313 A | 12/1999 | Shimmick et al. |
| 6,007,204 A | 12/1999 | Fahrenkrug et al. |
| 6,042,232 A | 3/2000 | Luce et al. |
| 6,043,885 A | 3/2000 | Mazuet et al. |
| 6,050,687 A | 4/2000 | Bille et al. |
| 6,086,204 A | 7/2000 | Magnante |
| 6,095,651 A | 8/2000 | Williams et al. |
| 6,096,077 A | 8/2000 | Callahan et al. |
| 6,155,684 A | 12/2000 | Bille et al. |
| 6,199,986 B1 | 3/2001 | Williams et al. |
| 6,251,101 B1 | 6/2001 | Glockler |
| 6,262,328 B1 | 7/2001 | Wicks et al. |
| 6,264,328 B1 | 7/2001 | Williams et al. |
| 6,270,221 B1 | 8/2001 | Liang et al. |
| 6,271,915 B1 | 8/2001 | Frey et al. |
| 6,275,718 B1 | 8/2001 | Lempert |
| 6,299,311 B1 | 10/2001 | Williams et al. |
| 6,299,618 B1 | 10/2001 | Sugiura |
| 6,338,559 B1 | 1/2002 | Williams et al. |
| 6,379,005 B1 | 4/2002 | Williams et al. |
| 6,382,793 B1 | 5/2002 | Lai et al. |
| 6,382,794 B1 | 5/2002 | Lai et al. |
| 6,382,795 B1 | 5/2002 | Lai |
| 6,394,605 B1 | 5/2002 | Campin et al. |
| 6,409,345 B1 | 6/2002 | Molebny et al. |
| 6,419,671 B1 | 7/2002 | Lemberg |
| 6,439,720 B1 | 8/2002 | Graves et al. |
| 6,460,997 B1 | 10/2002 | Frey et al. |
| 6,497,483 B2 | 12/2002 | Frey et al. |
| 6,508,812 B1 | 1/2003 | Williams et al. |
| 6,550,917 B1 | 4/2003 | Neal et al. |
| 6,561,648 B2 | 5/2003 | Thomas |
| 6,570,143 B1 | 5/2003 | Neil et al. |
| 6,572,230 B2 | 6/2003 | Levine |
| 6,575,572 B2 | 6/2003 | Lai et al. |
| 6,578,963 B2 | 6/2003 | Pettit |
| 6,585,723 B1 | 7/2003 | Sumiya |
| 6,588,902 B2 | 7/2003 | Isogai |
| 6,598,975 B2 | 7/2003 | Liang et al. |
| 6,601,956 B1 | 8/2003 | Jean et al. |
| 6,609,793 B2 | 8/2003 | Norrby et al. |
| 6,609,794 B2 | 8/2003 | Levine |
| 6,626,535 B2 | 9/2003 | Altmann |
| 6,626,538 B1 | 9/2003 | Arrowsmith |
| 6,634,751 B2 | 10/2003 | Turner et al. |
| 6,637,884 B2 | 10/2003 | Martino |
| 6,658,282 B1 | 12/2003 | Eagan et al. |
| 6,679,606 B2 | 1/2004 | Campin et al. |
| 6,685,319 B2 | 2/2004 | Watson et al. |
| 6,702,806 B2 | 3/2004 | Gray et al. |
| 6,705,729 B2 | 3/2004 | Piers et al. |
| 6,736,509 B2 | 5/2004 | Martino et al. |
| 6,736,510 B1 | 5/2004 | Van Heugten |
| 6,739,721 B2 | 5/2004 | Altmann |
| 6,761,454 B2 | 7/2004 | Lai et al. |
| 6,781,681 B2 | 8/2004 | Horwitz |
| 6,786,603 B2 | 9/2004 | Altmann |
| 6,793,654 B2 | 9/2004 | Lemberg |
| 6,819,413 B2 | 11/2004 | Neal et al. |
| 6,827,444 B2 | 12/2004 | Williams et al. |
| 6,836,374 B2 | 12/2004 | Esch et al. |
| 6,905,641 B2 | 6/2005 | Platt et al. |
| 6,908,196 B2 | 6/2005 | Herekar et al. |
| 6,926,710 B2 | 8/2005 | Cox et al. |
| 6,948,818 B2 | 9/2005 | Williams et al. |
| 6,997,555 B2 | 2/2006 | Dick et al. |
| 7,018,376 B2 | 3/2006 | Webb |
| 7,034,949 B2 | 4/2006 | Horwitz |
| 7,044,602 B2 | 5/2006 | Chernyak |
| 7,044,604 B1 | 5/2006 | Arrowsmith |
| 7,057,806 B2 | 6/2006 | Atkinson |
| 7,066,928 B2 | 6/2006 | Dick et al. |
| 7,068,439 B2 | 6/2006 | Esch et al. |
| 7,070,276 B2 | 7/2006 | Koretz |
| 7,077,522 B2 | 7/2006 | Williams |
| 7,111,938 B2 | 9/2006 | Andino et al. |
| 7,182,780 B2 | 2/2007 | Terwee et al. |
| 7,237,898 B1 | 7/2007 | Hohla et al. |
| 7,255,442 B2 | 8/2007 | Bucourt et al. |
| 7,303,281 B2 | 12/2007 | Wakil et al. |
| 7,336,371 B1 | 2/2008 | Haidner et al. |
| 7,341,348 B2 | 3/2008 | Eagan |
| 7,350,916 B2 | 4/2008 | Hong et al. |
| 7,350,920 B2 | 4/2008 | Levine |
| 7,357,509 B2 | 4/2008 | Williams et al. |
| 7,377,641 B2 | 5/2008 | Piers et al. |
| 7,380,942 B2 | 6/2008 | Molebny et al. |
| 7,401,919 B2 | 7/2008 | Vogelsang et al. |
| 7,406,263 B2 | 7/2008 | Graves et al. |
| 7,416,305 B2 | 8/2008 | Williams et al. |
| 7,425,067 B2 | 9/2008 | Warden et al. |
| 7,441,901 B2 | 10/2008 | Liang |
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |

(56) References Cited

U.S. PATENT DOCUMENTS

| | | |
|---|---|---|
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,988,291 B2 | 8/2011 | Ianchulev |
| 8,002,410 B2 | 8/2011 | Shea |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0105044 A1 | 5/2005 | Warden et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1 | 1/2006 | Mayo et al. |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0236702 A1 | 10/2007 | Neal et al. |
| 2007/0260157 A1 | 11/2007 | Norrby |
| 2008/0004610 A1* | 1/2008 | Miller et al. ............ 606/6 |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0036386 A1 | 2/2010 | Ianchulev |
| 2010/0042210 A1 | 2/2010 | Ianchulev |
| 2011/0267579 A1 | 11/2011 | Van Heugten |
| 2012/0147460 A1 | 6/2012 | Kubler |

FOREIGN PATENT DOCUMENTS

| | | |
|---|---|---|
| CN | 2010-80040737.6 | 6/2011 |
| DE | 43 10 561 A1 | 9/1994 |
| EP | 0931504 A1 | 7/1999 |
| EP | 2444021 | 4/2012 |
| EP | 2453822 | 5/2012 |
| EP | 2453823 | 5/2012 |
| EP | 1596710 | 1/2013 |
| GB | 1 209 451 | 10/1970 |
| IL | 138282 | 7/2004 |
| JP | 11-24434 | 5/1989 |
| JP | 9-122075 | 5/1997 |
| JP | 10-272100 | 10/1998 |
| JP | 2000-139996 | 5/2000 |
| JP | 2001-507258 A | 6/2001 |
| JP | 2001-314372 A | 11/2001 |
| JP | 2002-306418 A | 10/2002 |
| JP | 2003-509731 A | 3/2003 |
| JP | 2003-102689 A | 4/2003 |
| JP | 4972546 | 4/2012 |
| WO | WO 92/01417 | 2/1992 |
| WO | WO 96/22506 | 7/1996 |
| WO | WO 98/27863 | 7/1998 |
| WO | WO 01/06914 | 2/2001 |
| WO | WO 01/21061 | 3/2001 |
| WO | WO 01/26591 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 | 6/2003 |
| WO | WO 03/102498 | 12/2003 |
| WO | WO 2004/093663 | 11/2004 |
| WO | WO 2005/057252 | 6/2005 |
| WO | WO 2006/081031 | 8/2006 |
| WO | WO 2009/086059 | 7/2009 |

OTHER PUBLICATIONS

Office Action issued on Mar. 26, 2012 in connection with European Application No. EP 05737636.

Notice of Allowance issued on Aug. 6, 2012 in connection with corresponding U.S. Appl. No. 12/206,974, filed Sep. 9, 2008.

Non-Final Office Action issued on Aug. 24, 2012 in corresponding U.S. Appl. No. 12/835,668.

Preliminary Amendment filed on Sep. 14, 2012 in corresponding U.S. Appl. No. 13/750,080.

Notice of Allowance issued on Sep. 17, 2012 in corresponding Canadian Application No. CA 2,515,010.

Response to Office Action dated Mar. 26, 2012, mailed on Oct. 4, 2012 in corresponding Application No. EP 05737636.

Non-Final Office Action issued on Oct. 5, 2012 in U.S. Appl. No. 12/835,665.

Request for Continued Examination filed on Oct. 10, 2012 in corresponding U.S. Appl. No. 13/021,594.

Office Action issued on Oct. 25, 2012 in connection with corresponding U.S. Appl. No. 12/581,074.

Office Action issued on Oct. 26, 2012 in connection with corresponding U.S. Appl. No. 13/619,168.

Notice of Allowance issued on Oct. 30, 2012 in connection with corresponding U.S. Appl. No. 13/021,594.

Office Action issued on Nov. 5, 2012 in connection with corresponding U.S. Appl. No. 12/830,221.

(56) References Cited

OTHER PUBLICATIONS

Preliminary Amendment filed on Dec. 3, 2012 in corresponding U.S. Appl. No. 13/620,593.
Response to Office Action filed Dec. 10, 2012 in corresponding U.S. Appl. No. 12/740,753.
Office Action issued on Dec. 17, 2012 in corresponding U.S. Appl. No. 12/614,344.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations:" http://doctor-hill.com/iol-mail/piggyback.html, accessed on Feb. 12, 2010.
Aramberri, "Intraocular lens power circulation after corneal infrastructure surgery: Double-K method," J Cataract Refract Surg 29:2063-2067 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "Power of the Pre-Pupillary Pseudoshakos," B.J.O. 56:332-37 (1972).
Binkhorst, "The Optical Design of the Intraocular Lens Implants," Opthalmic Surg 6(3): 17-31 (1975).
Brandser R., "Accuracy of IOL calculation in cataract surgery", Acta Ophthalmol Scand. Apr. 1997; 75(2):162-5 (Abstract).
Castro et al., "Tilt and decentration of intraocular lenses in vivo from Purkinje and Scheimpflug imaging: Validation study," J. Cataract Refract. Surg. 2007; 33:418-429.
Chen et al., "Analysis of intraocular lens power calculation in post-radial keratotomy eyes," J Cataract Refract Surg 29:65-? (Jan. 2003).
Colenbrander, "Calculation of the Power of an Iris-Clip Lens for Distance Vision," Br J. Ophthal. 57:735-40(1973).
Cordonnier, M., et al., "How accurate is the hand-held refractor Retinomax(R) in measuring cycloplegic refraction: a further evaluation", Strabismus. Sep. 1998:6(3):133-I42 (Abstract).
Cua et al., Intraocular lens calculations in patients with corneal scarring and irregular astigmatism, J Cataract Refract Surg 29:1352-1357 (Jul. 2003).
Dalens H, Marcellier JJ, Moussiere L., "Use of the SRK (Sanders-Retzlaff-Kraft) regression formula in the preoperative calculation of the power of crystalline implants" (Abstract).
Donoso R., et al., "Emmetropization at cataract surgery. Looking for the best IOL power calculation formula according to the eye length", Arch Soc Esp Oftalmol. Sep. 2003:78(9):477-80 (Abstract).
El-Baha SM, et al., "Intraoperative biometry for intraocular lens (IOL) power calculation at silicone oil removal", Eur J Ophthalmol. Aug.-Sep. 2003;13(7):622-6. (Abstract).
El-Defrawy S., et al. "Evaluation of a hand-held autorefractor in children younger than 6", J Pediatr Ophthalmol Strabismus, 1998 ~ar-Apr;35(2):107-9 (Abstract).
Feiz, et al., "Intraocular Lens Power Calculation After Laser In Situ Keratomileusis for Myopia and Hyperopia—A Standard Approach," Cornea 20(8):792-797 (2001).
Feordorov et al. "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia. 2003;56(1):11-4 (Abstract).
Gernet, "IOL Calculation According to Gernet and the GOW 70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001).
Gimbel et al., "Accuracy and Predictability of Intraocular Lens Power Calculation After photorefractive keratectomy," J Cataract Refract Surg 26:1147-1151 (Apr. 2000).
Gupta, et al., "*Design and use of an infrared Pupilometer for real-time pupil mapping in response to incremental illumination levels,*" 2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/Article Standard/Article/detail/559856.
Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden Intraokularlinse" [Intraoperative retinoscopy for determining the refractive value of an implantable intraocular lens] Klin. Monatsbl. Augenheilkd. vol. 210, No. 4, 1997, pp. 207-212.
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," J. Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions. CLAO J. 1984, 10:326-31.
Holladay, JT, et al. "Calculating the Surgically Induced Refractive Change Following Ocular Surgery", J. Cataract Refract. Surg 1992; 18:429-43.
http://www.wavetecvision.com/ accessed Feb. 24, 2010.
Hunt et al., "Evaluation of the measurement of refractive error by the PowerRefractor: a remote, continuous and binocular measurement system of oculomotor function," Br. J. Opthalmol 87:1504-1508 (2003).
Ianchulev, "Method for Intraoperative Refractive IOL Calculation," Poster Presentation at Ophthalmology Conference (Apr. 2004)
Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536, Abstract.
Isenberg et al., "Use of the HARK Autorefractor in Children," American Journal of Ophthalmology 131(4):438-441 (2001).
Iuorno JD, et al., "Clinical comparison of the Welch Allyn SureSight handheld auto refractor versus cycloplegic auto refraction and retinoscopic refraction", J AAPOS, Apr. 2004;8(2):123-7 (Abstract).
Iwami S. et al., "Prediction of Postoperative Refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and LASIK", Korean J Ophthalmol. Jun. 2002;16(1):26-31 (Abstract).
Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).
Liang, et al. "Aberrations and Retinal Image Quality of the Normal Human Eye", J. Optical Society of America, vol. 14, No. 11, Nov. 1997.
Liang, et al. "Comparison of Measurements of Refractive Errors Between the Hand-held Retinomax and On-table Autorefractors in Cyclopleged and Noncyclopleged Children," American Journal of Ophthalmology 136(6): 1120-1128 (Dec. 2003).
Lipatov DV., "Assessment of the efficiency of different formulae applied to calculating the optic power of an intraocular lens in transscleral fixation", Vestn Oftalmol, Nov.-Dec. 2003; 119(6)3-5 (Abstract).

(56) References Cited

OTHER PUBLICATIONS

Ma, et al., "Simple method for accurate alignment in toric phakic and aphakic intraocular lens implantation," J Cataract Refract Surg, Technique, Oct. 2008, vol. 34, pp. 1631-1636.
Mackool RJ., "The cataract extraction-refraction-implantation technique for IOL power calculation in difficult cases", J Cataract Refract Surg. Apr. 1998;24(4):434-5 (Abstract).
Masket, et al., "Atlas of Cataract Surgery," Book cover in 1 page, Front Matter in 11 pages (Table of Contents in 3 pages), Chapter 19 pp. 147-158, Published by Martin Dunitz Ltd 1999, United Kingdom.
Methling D, Kalb G., "A New Program for Calculating Intraocular Lenses", Klin Monatsbl Augenheilkd. Oct. 1992;201 (4):247-53 (Abstract).
Moreno-Barriuso, et al., "Laser Ray Tracing Versus Hartmann-Shack Sensor for Measuring Optical Aberrations in the Human Eye", J. Optical Society of America, vol. 17, No. 6, Jun. 2000.
Nemeth et al., "Optical and ultrasound measurement of axial length and anterior chamber depth for intraocular lens power calculation," J Cataract Refract Surg 29:85-88 (Jan. 2003).
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001).
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Photograph of Oculus Instrument, accessed at http://www.oculus.de/en/sites/popup_bild_gross.php?news=&id=1056 on Apr. 29, 2011.
Quiroga, et al., "*Fourier transform method for automatic processing of moire deflectograms*," Jun. 1999, Society of Photo-Optical Instrumentation Engineers, pp. 974-982.
Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).
Retzlaff J., "A new intraocular lens calculation formula", J Am Intraocul Implant Soc. Apr. 1980 6(2):148-52. (Abstract).
Rosales et al., "Phakometry and lens tilt and decentration using a custom-developed Purkinje imaging apparatus: validation and measurements," Journal of the Optical Society of America, vol. 23, No. 3, Mar. 2006, pp. 509-520.
Rubin A., et al., "Refractive variation during autorefraction: multivariate distribution of refractive status", Optom Vis Sci. Jun. 1995;72(6):403-10 (Abstract).
Rubin A., et al., "Variation during autorefraction: influence of two different target types", Ophthalmic Physiol Opt Jan. 1997;17(1):38-43 (Abstract).
Sanders et al., "Comparison of the SRK/T formula and other theoretical and regression formulas," J Cataract Refract Surg. 16:341-346 (May 1990).
Sanders et al., "Comparisons of the SRK™ formula and other second generation formulas," J Cataract Refract Surg 14;136-141 (Mar. 1988).
Senjo, et al., "Prediction of Postoperative Refraction Using Intraoperative Retinoscopy," Journal of Japanese Ophthalmological Society, 1999, vol. 103, No. 7, pp. 551-555, Abstract.
Siahmed K., et al., "Optic biometry in intraocular lense calculation for cataract surgery. Comparison with usual methods", J Fr Ophtalmol. Nov. 2001;24(9):922-6 (Abstract).
Siganos et al., "Autorefractometry after laser in situ keratomileusis," J Cataract Refract Surg 29:133-137 (Jan. 2003).
Supplemental Amendment filed Apr. 1, 2010 in U.S Appl. No. 11/110,968, filed Apr. 20, 2005.
Supplementary European Search Report for Application No. 05737636.0, Dated Mar. 19, 2009.
Steele, G., et al., "Cycloplegic auto refraction results in pre-school children using the Nikon Retinomax Plus and the Welch Allyn SureSight", Optom Vis Sci. Aug. 2003;80(8):573-7 (Abstract).
Straub et al., "*Design of a compact Shack-Hartmann aberrometr for real-time measurement of aberrations in human eyes,*" 2000 Optical Society of America, pp. 110-113.
Suto et al., "Adjusting intraocular lens power for sulcus fixation," J Cataract Refract Surg 29:1913-1917 (Oct. 2003).
Tabernero et al., "Instrument for measuring the misalignments of ocular surfaces," Optical Society of America, Oct. 30, 2006, vol. 14, No. 22.
Thall et al., "Linear Regression Software for Intraocular Lens Implant Power Calculation," American Journal of Ophthalmology 101:597-599 (May 1986).
Thijssen JM., "The emmetropic and the iseikonic implant lens: computer calculation of the' refractive power and its accuracy", Ophthalmologica. 1975;171 (6):467-86 (Abstract).
Thompson et al., "A New Posterior Chamber Intraocular Lens Formula for Axial Myopes," Ophthalmology 91(5): 484-488 (May 1984).
Tromans et al., "Accuracy of intraocular lens power calculation in paediatric cataract surgery," Br J Ophthalmol 85:939-941 (2001).
Tseng, et al., "Calculating the optimal rotation of a misaligned toric intraocular lens," J Catactact Refract Surg, Laboratory Science, Oct. 2008, vol. 34, pp. 1767-1772.
Uozato et al., "Intraoperative Confirmation Device for IOL Centering," Folia Ophthalmologica Japonica, vol. 41, 1990, pp. 1325-1329.
Villada Jr., et al., "Comparative evaluation of the Allergan Humphrey 570 and Canon RK-I autorefractors; II, Objective autorefraction in pseudophakes", Eye, 1992;6 (Pt 3):287-9 (Abstract).
Walline JJ, "Repeatability and validity of astigmatism measurements", J Refract Surg. Jan.-Feb. 1999; 15(1):23-31 (Abstract).
Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.
Wood IC., "A review of autorefractors", Eye. 1987;1 (Pt 4):529-35 (Abstract).
Yalvac IS, et al., "Calculation of intraocular lens power with the SRK IIformula for axial high myopia" Eur J Ophthalmol. Oct.-Dec. 1996;6(4):375-8 (Abstract).
Zaldivar et al., "Intraocular lens power calculations in patients with extreme myopia," J. Cataract Refract Surg 26:668-674 (May 2000).

\* cited by examiner

| Corneal Refraction | | | Toric Lens Power & Axis | | Refraction Measurement | | | Recommended Rotation | | Measurement Axis versus lens axis | |
|---|---|---|---|---|---|---|---|---|---|---|---|
| Sph | Cyl | Axis | Cylinder | Axis | Sph | Cyl | Axis | Clockwise | Counter Clockwise | Clockwise | Counter Clockwise |
| -1.00 | +2.50 | 80 | -2.08 | 100 | -1.59 | 1.61 | 52 | 20 | | | 48 |
| | | | | 90 | -1.23 | 0.90 | 64 | 10 | | | 36 |
| | | | | 85 | -1.08 | 0.59 | 61 | 6 | | | 24 |
| | | | | 80 | -1.00 | 0.44 | 80 | 0 | | | 0 |
| | | | | 75 | -1.08 | 0.59 | 99 | | | | |
| | | | | 70 | -1.23 | 0.90 | 106 | | | | |
| | | | | 60 | -1.59 | 1.61 | 108 | | | | |
| -0.50 | +2.00 | 45 | -1.55 | 90 | -1.54 | 2.53 | 26 | 45 | | | 64 |
| | | | | 80 | -1.31 | 2.07 | 23 | 35 | | | 57 |
| | | | | 70 | -1.05 | 1.55 | 20 | 25 | | | 50 |
| | | | | 60 | -0.78 | 1.02 | 20 | 15 | | | 40 |
| | | | | 50 | -0.55 | 0.54 | 30 | 5 | | | 20 |
| | | | | 45 | -0.50 | 0.45 | 45 | 0 | | | 0 |
| -0.50 | +2.00 | 110 | -1.03 | 140 | -0.88 | 1.73 | 95 | 30 | | | 45 |
| | | | | 130 | -0.71 | 1.38 | 96 | 20 | | | 34 |
| | | | | 120 | -0.56 | 1.09 | 101 | 10 | | | 19 |
| | | | | 115 | -0.52 | 1.02 | 105 | 5 | | | 10 |
| | | | | 110 | -0.50 | 0.97 | 110 | 0 | | | 0 |
| -1.00 | +0.60 | 75 | -1.03 | 90 | -1.01 | 0.59 | 15 | 15 | 0 | 75 | 97 |
| | | | | 85 | -0.97 | 0.51 | 7 | 10 | 5 | 78 | 90 |
| | | | | 80 | -0.94 | 0.45 | 177 | 5 | 10 | | 83 |
| | | | | 75 | -0.93 | 0.43 | 165 | 0 | 15 | | 78 |
| | | | | 70 | -0.94 | 0.45 | 153 | | | | 75 |
| | | | | 65 | -0.97 | 0.51 | 143 | | | | |
| | | | | 60 | -1.01 | 0.59 | 135 | | | | |
| -0.75 | +4.00 | 90 | -2.06 | 115 | -1.51 | 3.46 | 75 | 25 | | | 40 |
| | | | | 105 | -1.00 | 2.44 | 78 | 15 | | | 27 |
| | | | | 95 | -0.78 | 2.00 | 85 | 5 | | | 10 |
| | | | | 90 | -0.75 | 1.94 | 90 | 0 | | | 0 |

FIG. 16

OPTICAL ANGULAR MEASUREMENT SYSTEM FOR OPHTHALMIC APPLICATIONS AND METHOD FOR POSITIONING OF A TORIC INTRAOCULAR LENS WITH INCREASED ACCURACY

CROSS-REFERENCE TO RELATED APPLICATIONS

This application is a continuation of U.S. patent application Ser. No. 12/614,344, filed Nov. 6, 2009, and entitled, "OPTICAL ANGULAR MEASUREMENT SYSTEM FOR OPHTHALMIC APPLICATIONS AND METHOD FOR POSITIONING OF A TORIC INTRAOCULAR LENS WITH INCREASED ACCURACY," which claims priority to the following U.S. provisional patent applications: U.S. Provisional Patent Application 61/166,660, filed Apr. 3, 2009, and entitled "OPTICAL ANGULAR MEASUREMENT SYSTEM FOR OPHTHALMIC APPLICATIONS"; and U.S. Provisional Patent Application 61/112,148, filed Nov. 6, 2008, and entitled "POSITIONING OF A TORIC INTRAOCULAR LENS WITH INCREASED ACCURACY." All of the foregoing priority applications are hereby incorporated herein by reference in their entirety to be considered part of this specification

BACKGROUND OF THE INVENTION

1. Field of the Invention

The field of the invention relates to ophthalmic equipment and procedures, such as, for example, equipment and procedures for performing cataract surgery.

2. Description of the Related Art

Certain ophthalmic procedures involve angular measurements of or on the eye. One ophthalmic procedure that generally involves angular measurements of the eye is a cataract surgery. Cataracts are clouded regions that can develop in the natural crystalline lens of an eye. A cataract can range in degree from slight clouding to complete opacity. Typically, formation of cataracts in human eyes is an age-related process. If left untreated, cataracts can lead to blindness. Surgeries have been developed for the treatment of cataracts. Typically, an incision is made in the eye and the natural crystalline lens is removed. An artificial lens called an intraocular lens (IOL) is then inserted in the capsular bag of the eye in place of the natural crystalline lens. The spherical optical refractive power of the IOL implant may be selected, for example, so as to place the eye in a substantially emmetropic state when combined with the refractive power of the cornea of the eye.

A cataract surgery typically requires a phaco incision, through which the patient's natural crystalline lens is removed and an artificial intraocular lens (IOL) is inserted, to be made at the limbus of a patient's eye. In some cases, it may be advantageous for this phaco incision to be made along a meridian at some specified angular orientation on the eye. Thus, the angular location of the phaco incision is measured in some way.

Cataract surgeries, and other ophthalmic procedures, may also involve additional angular measurements. For example, a cataract surgery may involve angular measurements so that the surgeon can align a toric IOL to a particular angular orientation. Toric IOL implants provide a degree of correction for any regular astigmatism which may exist in the patient's cornea. Such regular astigmatism results from a difference in the degree of curvature of the cornea in orthogonal meridians such that the eye has different focal lengths for light incident upon it in each of the planes of the two orthogonal meridians. Regular astigmatism has an axis associated with it that indicates its angular orientation.

A toric IOL implant has spherical and cylindrical refractive power. The cylindrical refractive power of the toric IOL more effectively corrects corneal astigmatism if it is accurately aligned with the angular orientation of the corneal astigmatism of the patient's eye. Therefore, there is a need for systems and methods capable of accurately determining the axis of cylindrical refractive power in the cornea to which the toric IOL implant should be aligned. In addition, there is a need for systems and methods that allow for more accurate positioning of the toric IOL implant at the optimal angular orientation for correction of the astigmatic power of the cornea.

An ophthalmic surgery may also involve Limbal Relaxing Incisions (LRI) to be performed in an effort to correct corneal astigmatism. Even once the desired angular locations for these incisions have been determined, the surgeon still needs some means for actually identifying the desired angular locations on the eye. Other ophthalmic procedures may also involve certain angular measurements of the eye to be made.

SUMMARY OF THE INVENTION

In some embodiments, an ophthalmic system comprises: an optical refractive power measurement device for measuring at least the cylindrical power and axis of a patient's eye, the optical refractive power measurement device having a first optical pathway along a first optical axis; and an optical angular measurement device in a fixed spatial relationship with the optical refractive power measurement device, the optical angular measurement device being configured to provide an angular indicia for performing angular measurements or alignments with respect to the patient's eye, the optical angular measurement device having a second optical pathway along a second optical axis.

In some embodiments, a method for aligning the astigmatic axis of a toric IOL with the astigmatic axis of the cornea of a patient's eye during cataract surgery comprises: determining a first magnitude and axis of the corneal astigmatism; removing the natural lens; inserting a toric IOL; deliberately misaligning the astigmatic axis of the toric IOL by at least 15° from the first astigmatic axis of the cornea; and intra-operatively measuring the total refractive power of the pseudophakic eye while the toric IOL is deliberately misaligned.

In some embodiments, a method for aligning the astigmatic axis of a toric IOL with the astigmatic axis of the cornea of a patient's eye during cataract surgery comprises: removing the natural lens from the patient's eye; intra-operatively measuring the refractive power of the patient's aphakic eye; determining the magnitude and axis of the patient's corneal astigmatism based on the intra-operative aphakic measurement; inserting a toric IOL; and rotating the toric IOL so that its astigmatic axis is aligned with the axis of the patient's corneal astigmatism.

In some embodiments, a method for aligning the astigmatic axis of a toric IOL with the astigmatic axis of the cornea of a patient's eye during cataract surgery comprises: removing the natural lens from the patient's eye; inserting a toric IOL into the eye at a first angular orientation through a phaco incision; intra-operatively measuring the total refractive power of the patient's pseudophakic eye while the toric IOL is positioned at the first angular orientation; rotating the toric IOL to a second angular orientation prior to completion of the cataract surgery; and intra-operatively measuring the total refractive power of the patient's pseudophakic eye while the toric IOL is positioned at the second angular orientation.

In some embodiments, a computer for use in performing cataract surgery is programmed to perform a method comprising: electronically receiving a first input comprising a first magnitude and astigmatic axis of a toric IOL after it has been implanted in the eye of a patient; electronically receiving a second input comprising an intra-operatively measured second magnitude and axis of the astigmatism of a pseudophakic eye that comprises the toric IOL; and electronically calculating a third magnitude and axis of astigmatism based on the first and second inputs.

In some embodiments, a computer for use in performing cataract surgery is programmed to perform a method comprising: electronically receiving a first input comprising an intra-operatively measured first magnitude and axis of the astigmatism of a pseudophakic eye that comprises a toric IOL positioned at a first angular orientation; electronically receiving a second input comprising an intra-operatively measured second magnitude and axis of the astigmatism of the pseudophakic eye with the toric IOL positioned at a second angular orientation; and electronically calculating a third magnitude and axis of astigmatism based on the first and second inputs.

In some embodiments, a method for aligning the astigmatic axis of a toric IOL with the astigmatic axis of the cornea of a patient's eye during cataract surgery comprises: removing the natural lens from the patient's eye; intra-operatively measuring the refractive power of the patient's aphakic eye; determining the magnitude and axis of the patient's corneal astigmatism based on the intra-operative aphakic measurement; inserting a toric IOL; intra-operatively measuring the refractive power of the patient's pseudophakic eye; and determining whether the astigmatic axis of the toric IOL is correctly aligned with the axis of the patient's corneal astigmatism based on the intraoperative pseudophakic measurement.

BRIEF DESCRIPTION OF THE DRAWINGS

For purposes of summarizing the disclosure, certain aspects, advantages and features of the invention are described herein. Certain embodiments are illustrated in the accompanying drawings, which are for illustrative purposes only.

FIG. 16 is a table illustrating the effects of misalignment of a toric IOL on the residual astigmatism of several example patients undergoing cataract surgery.

DETAILED DESCRIPTION OF THE PREFERRED EMBODIMENT

Various embodiments of an optical angular measurement system for projecting an image of an angular measurement reticle, or other angular measurement and/or alignment indicia, onto the eye of a patient, or for superimposing an image of the angular measurement reticle, or other angular measurement and/or alignment indicia, onto an image of the patient's eye, for example, are described herein in conjunction with the accompanying drawings. Also described herein are various methods and devices for aligning the astigmatic axis of a toric IOL with the astigmatic axis of the cornea of a patient's eye during cataract surgery. It should be understood that the embodiments described and illustrated herein are provided for illustrative purposes and should not be construed as limiting. Not necessarily all described features and advantages of the various embodiments are achieved in accordance with any one particular embodiment of the invention. Thus, the invention may be embodied or carried out in a manner that achieves or optimizes one advantage or group of advantages as taught herein without necessarily achieving other advantages as may be taught herein.

Optical Angular Measurement Systems

Figure 1:
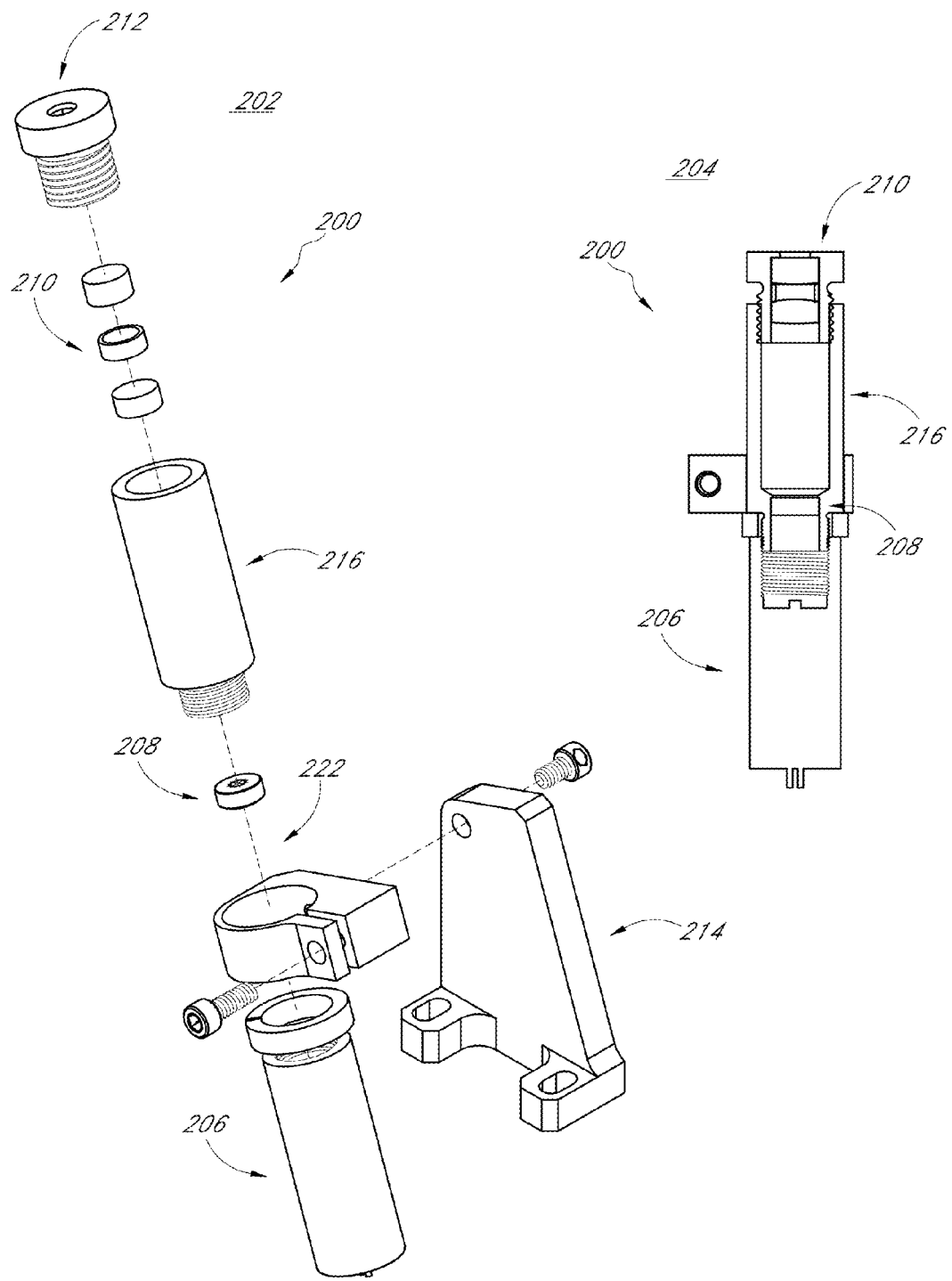
FIG. 1 includes a perspective exploded view of an embodiment of an optical angular measurement system for projecting an image of an angular measurement reticle onto a patient's eye, as well as a cut-away view of the optical angular measurement system.

FIG. 1 includes a perspective exploded view 202 of an embodiment of an optical angular measurement system 200 for projecting an image of an angular measurement reticle 208 onto a patient's eye. FIG. 1 also includes a cutaway view 204 of the optical angular measurement system 200. The optical angular measurement system 200 can be used, for example, to perform angular measurements and/or alignments with respect to a patient's eye (e.g., angular measurements of, on, or in the patient's eye). In some embodiments, the optical angular measurement system 200 includes a light source 206, an angular measurement reticle 208, an imaging lens 210, and an output aperture 212. The optical angular measurement system 200 may also include a mounting bracket 214 for mounting the optical angular measurement system 200 to a support structure, or ophthalmic instrument, that fixedly supports the optical angular measurement system 200 spatially with respect to a patient's eye such that an image of the angular measurement reticle 208 is projected onto the eye. The optical components of the optical angular measurement system 200 may be mounted within a housing 216, such as a lens tube or the like.

The optical angular measurement system 200 projects, for example, a graphical pattern onto the patient's eye. In some embodiments, this graphical pattern is an image of the angular measurement reticle 208 and is viewable by a surgeon who is performing an ophthalmic surgical procedure on the eye. The graphical pattern may include, for example, radial angular graduation marks that allow the surgeon to make angular measurements of the eye during the surgical procedure and/or to locate specific angular positions on the surface of or in the eye, for example, for purposes of aligning surgical implants to specific angular orientations or for performing surgical acts, such as incisions, etc.

For example, the optical angular measurement system 200 can be used to measure the absolute angle between a first ocular feature located along a first meridian and a second ocular feature located along a second meridian of the eye (e.g., the angle between two features or positions on the cornea or limbus, or between the meridians upon which they lie). It can also be advantageously used to measure or determine a relative angle between, for example, an ocular feature and a reference point or reference meridian on the eye. The optical angular measurement system 200 can be used to identify a location or meridian that is angularly separated by a predetermined amount from an ocular feature, reference point, or reference meridian (e.g., to identify a location on the cornea that is 30° clockwise from a 0° reference point on a 0°-180° horizontal reference meridian). In addition, the optical angular measurement system 200 can be used to measure the angular orientation of an ophthalmic instrument (e.g., about the instrument's optical axis) with respect to the eye. The optical angular measurement system 200 can additionally be used for some, if not all, of the same purposes as a Mendez degree gauge.

These and other angular measurements of the eye, which can be made by the optical angular measurement system 200, can be used for a number of purposes during ophthalmic procedures which include, but are not limited to, the following: determining the appropriate angular location or orientation to make an incision (e.g., phaco incision or LRI); angularly or rotationally aligning an ocular implant, such as a toric IOL, within the patient's eye to a desired angular orientation; angularly or rotationally aligning an optical instrument external to the patient's eye; determining the appropriate angular location to make an alignment mark on the eye, etc.

In some embodiments, the projected image of the angular measurement reticle 208 allows the doctor to utilize both hands during the surgical procedure and may, under some circumstances, eliminate the need for a hand-held instrument, such as a Mendez degree gauge, for performing such angular measurements. This is a significant advantage because it frees up both of the surgeon's hands to perform tasks that may have previously been awkward or even impossible to perform while making angular measurements of the eye using a hand-held device. This facilitates the surgeon's ability to quickly and accurately perform angular measurements and alignments during surgery and to accurately complete a corrective procedure. Another advantage of the optical angular measurement system 200 is that, unlike a Mendez degree gauge, it does not physically apply pressure to the eye, thereby increasing the patient's comfort level during surgery.

In some embodiments, the light source 206 outputs monochromatic or polychromatic visible light, though in either case it may be advantageous for the light output by the light source 206 to have good contrast with the colors and features of the eye so that it is plainly viewable on the eye. In some embodiments, the light source 206 outputs white light, while in other embodiments it outputs red light or green light. In still other embodiments, the light source 206 can output other colors. The light source 206 can output coherent or incoherent light. The light can be collimated or not. In some embodiments, the light source 206 is a light emitting diode (LED) or lamp, such as a halogen lamp or a xenon arc lamp. The intensity of the light output by the light source 206 is preferably bright enough to be clearly seen on the patient's eye by the surgeon but not so intense as to harm the tissues of the eye.

The light source 206 outputs light along an optical pathway generally along an optical axis 222 towards the angular measurement reticle 208. In some embodiments, the optical axis 222 is coincident with the visual axis of the patient's eye when the patient is looking forward, but this is not required. For example, in some embodiments, the optical axis 222 of the optical angular measurement system 200 is laterally offset from the visual axis of the eye, angularly offset from the visual axis of the eye, and/or the two axes are skew to one another. In some embodiments, however, these offsets are sufficiently small so as not to appreciably affect the image of the angular measurement reticle 208 that is formed on the patient's eye.

The light from the light source 206 may be transmitted directly to the angular measurement reticle 208, or the optical angular measurement system 200 may additionally include other optical elements between the light source 206 and the angular measurement reticle 208. For example, a diffuser may be located between the light source 206 and the angular measurement reticle 208 in order to more uniformly illuminate the reticle 208. In addition, in some embodiments, the optical angular measurement system 200 may include a lens between the diffuser and the angular measurement reticle 208 so as to, for example, image the diffuser onto the reticle. This may further improve the uniformity of the illumination of the reticle 208.

The light source 206 can also be a laser. The laser may output a collimated beam of light whose diameter is comparable to the diameter of the angular measurement reticle 208 such that the laser light fully illuminates the reticle. In some embodiments, the light source 206 may output a relatively narrow beam of laser light which then passes through a beam expander to increase the size of the beam so that it fully illuminates the reticle 208. Other methods of illuminating the angular measurement reticle 208 can also be used.

In some embodiments, the angular measurement reticle 208 has generally transparent or relatively optically transmissive portions, and generally opaque or relatively optically absorptive portions. The angular measurement reticle 208 may be, for example, a sheet of opaque material with an optically transmissive pattern formed in or through the material. For example, the angular measurement reticle 208 may be a sheet of opaque metal or plastic with a pattern that is physically cut out from the material such that light passes through the pattern. In such embodiments, one consideration is that the transmissive portion of the angular measurement reticle 208 be large enough to pass a sufficient amount of light to be clearly visible upon the patient's eye without requiring an unduly bright light source 206.

In other embodiments, the angular measurement reticle 208 is a sheet of generally optically transmissive material, such as glass or plastic, with an opaque, or relatively absorptive, pattern formed on or in the material. For example, the pattern may be formed by depositing an opaque coating on the generally transmissive angular measurement reticle 208 in the shape of the pattern, or by etching the pattern into the reticle 208. In still other embodiments, the angular measurement reticle 208 can be a generally opaque pattern suspended in air such as, for example, a circular frame to which one or more wires are attached and stretched across the interior void of the frame. In some embodiments, the pattern formed in the angular measurement reticle 208 is centered on the optical axis 222 and is generally radially and/or azimuthally symmetric.

In some embodiments, the angular measurement reticle 208 is a transmissive or reflective spatial light modulator, such as a mask with a controllable mask pattern. For example, the angular measurement reticle 208 can be made up of an array of modulators that can be individually controlled to block, pass, or reflect light, such as a liquid crystal array or display. In some embodiments, the angular measurement reticle 208 is communicatively coupled with a computer such that the computer can controllably alter various features of the angular measurement reticle, even during an ophthalmic procedure, by altering the states of the various modulators that make up the controllable mask reticle. For example, the computer can change the pattern of the reticle 208, the intervals between angular graduation marks, or the orientation of an alignment indicator, among other things. In addition, or alternatively, the computer could also be linked to an optical refractive power measurement device (e.g., a wavefront aberrometer) so as to be able to display on the angular measurement reticle 208 additional information such as the refractive power of the patient's eye, or other useful information. In addition, or alternatively, the reticle can display any type of relevant information from any other source. In some embodiments, input to alter a controllable mask angular measurement reticle 208 can be provided by a surgeon via a user interface, or automatically from some other ophthalmic device depending upon, for example, a measurement that has been performed, the type of ophthalmic procedure, etc.

Figure 2:
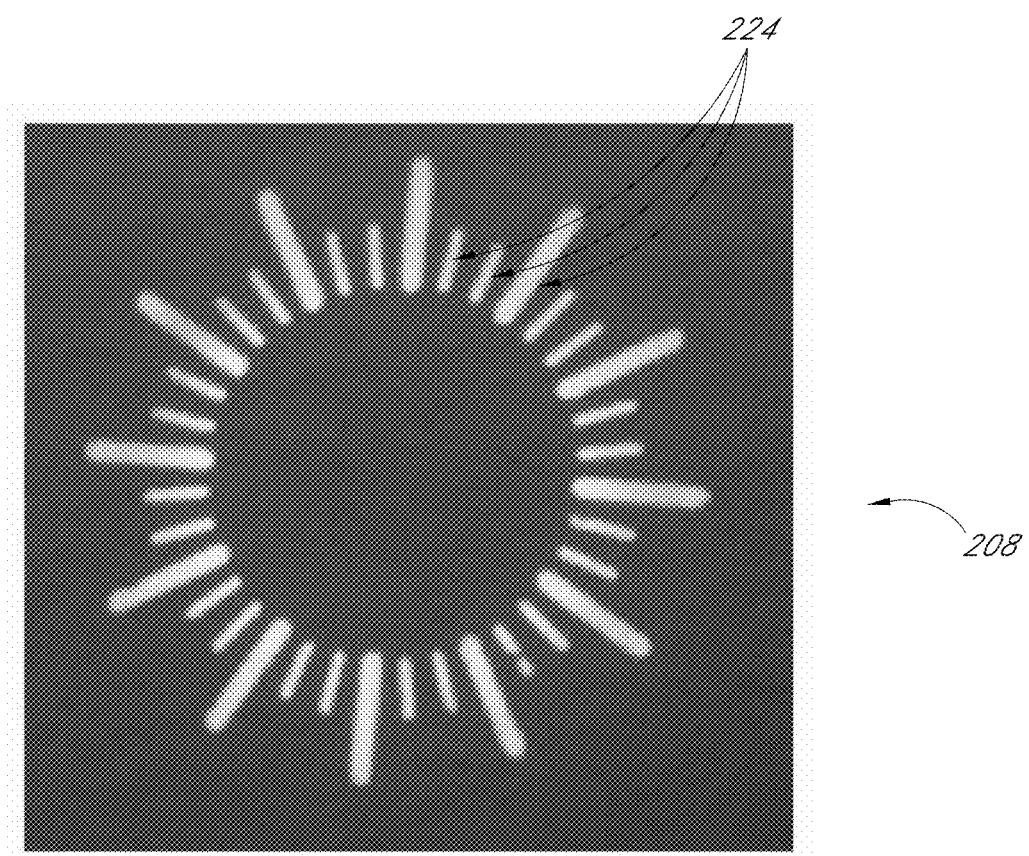
FIG. 2 illustrates an embodiment of an angular measurement reticle to be imaged onto a patient's eye using, for example, the optical angular measurement system of FIG. 1.

FIG. 2 illustrates an embodiment of an angular measurement reticle 208 to be imaged onto a patient's eye using, for example, the optical angular measurement system 200 of FIG. 1. In some embodiments, the angular measurement reticle 208 has a pattern that includes a plurality of angular graduation marks 224. In some embodiments, the angular graduation marks are arranged regularly in a complete circle from 0° to 360°. In other embodiments, the angular graduation marks cover only a subset, or multiple subsets, of the 360° range. In some embodiments, angular graduation marks are formed at intervals or sub-intervals of at least every 90°, at least every 60°, at least every 45°, at least every 30°, at least every 20°, at least every 15°, at least every 10°, at least every 5°, or at least every 1° over the angular range of the graduation marks. The angular graduation marks may comprise, for example, line segments, arrows, spots, or other shapes. In some embodiments, the angular measurement reticle pattern may also include alphanumeric characters, designs, logos, alignment indicators, etc.

In the case of the embodiment of the angular measurement reticle 208 shown in FIG. 2, there are 36 angular graduation marks 224 arranged at 10° intervals. The angular graduation marks located at 30° intervals are represented by longer line segments, while the intermediate 10° intervals are represented by shorter line segments. In general, however, the angular graduation marks 224 could have many different styles, depending upon, for example, aesthetic qualities or the type of surgical procedure being performed. While the angular graduation marks 224 shown in FIG. 2 are uniformly angularly spaced, in general, this is not required and the angular graduation marks 224 could instead be irregularly spaced such as, for example, by omitting angular graduation marks at certain angles or by spacing the angular graduation at intervals of varying numbers of degrees.

The angular measurement reticle 208 may be configured so that a multi-color image of the reticle is projected upon the patient's eye. For example, the light source 206 may output white, or other polychromatic light. Sub-portions of the optically transmissive reticle may include differently colored optical filters so that the polychromatic light from the light source 206 which passes through the reticle 208 is filtered by wavelength and is ultimately imaged upon the patient's eye in a multi-colored image. Different colors can be advantageously used to distinguish different angular graduation marks, alignment indicators, alphanumeric information, etc.

In some embodiments, the angular measurement reticle 208 is removable to allow for installation of a replacement reticle having a different pattern. This may be useful, for example, if certain patterns on the angular measurement reticle 208 are differently suited to the various surgical procedures that can be performed using the optical angular measurement system 200. In addition, in some embodiments the angular measurement reticle 208, or a portion of it, is rotatable, either manually or in an automated fashion using a motor or the like. For example, the angular measurement reticle 208 may include a first portion with angular graduation marks 224, and a second portion with one or more alignment indicators. In some embodiments, the second portion of the angular measurement reticle 208 associated with an alignment indicator may be rotatable with respect to the first portion of the reticle that is associated with the angular graduation marks 224.

An angular measurement reticle 208 with a rotatable alignment mark may be advantageous in situations where the system 200 is used in a procedure to insert an ocular implant, such as, for example, a toric IOL. As described herein, an ocular implant such as a toric IOL is advantageously aligned to a specific angular orientation in order to provide good refractive correction. More about the insertion and alignment of toric IOLs is described herein. The angular measurement reticle 208 may include a rotatable alignment indicator that is distinguishable from the angular graduation marks 224 (e.g., a line segment or arrow of different shape, length, or color) and that can be a used as a guide for the surgeon to properly orient the ocular implant. In such cases, once the desired angular orientation of the optical implant has been determined, the alignment indicator can be rotated, for example with respect to the angular graduation marks 224, so that it is located at the desired angular orientation for the optical implant. Again, this can be done manually by the surgeon, or automatically using a stepper motor or the like with an appropriate automated control system. The surgeon can then use the alignment indicator, an image of which may be projected upon the patient's eye, as a guide for correctly orienting the ocular implant (e.g., for aligning the astigmatic axis of a toric IOL with the axis of corneal astigmatism of the patient's eye).

In some embodiments, the optical angular measurement system 200 may include other types of angular alignment guides or indicia in place of or in addition to a reticle. For example, in some embodiments, the optical angular measurement system uses a static or dynamic holographic optical element (HOE) to project an angular alignment image onto the patient's eye. In some embodiments, spinning mirrors, acousto-optic modulators, or electro-optic modulators can be used to rapidly and repetitively draw out an angular alignment image on the patient's eye, for example, by controllably scanning a laser beam over the eye. In still other embodiments, one or more cylindrical lenses can be substituted for the angular measurement reticle 208 and the focusing lenses 210. When the one or more cylindrical lenses are illuminated by the light source 206, they will, if designed with the appropriate focal length, project one or more lines, each line corresponding to a cylindrical lens, onto the surface of the patient's eye in a pattern (e.g., a radial and/or azimuthal pattern). If there are a plurality of cylindrical lenses angularly rotated with respect to one another about the optical axis 222, then the projected lines will be similarly rotated and can serve as angular measurement indicia. Similarly, a plurality of spherical lenses could be used in place of the angular measurement reticle 208 and the focusing lenses 210 to project a plurality of spots onto the patient's eye in a pattern (e.g., a radial pattern) that can indicate angular measurements to the surgeon. A benefit of such embodiments without the angular measurement reticle 208 is that relatively little, if any, light from the light source 206 is wasted by having been blocked by a reticle. Thus, it is possible that a lower-power light source can be used. Other components can also be used to create the angular measurement indicia.

In some embodiments, at least a portion of the light that is incident upon the angular measurement reticle 208 passes through the reticle to the imaging lens 210. The imaging lens 210 may have a single lens element or multiple lens elements. For example, in some embodiments the imaging lens 210 includes an achromatic doublet element and one additional spherical lens. The lens elements can be made of many different optical materials, such as various types of glass and plastic, which are known in the art. In some embodiments, the imaging lens 210 may also include aspheric lens elements or other optical elements commonly used in imaging applications.

Figure 3:
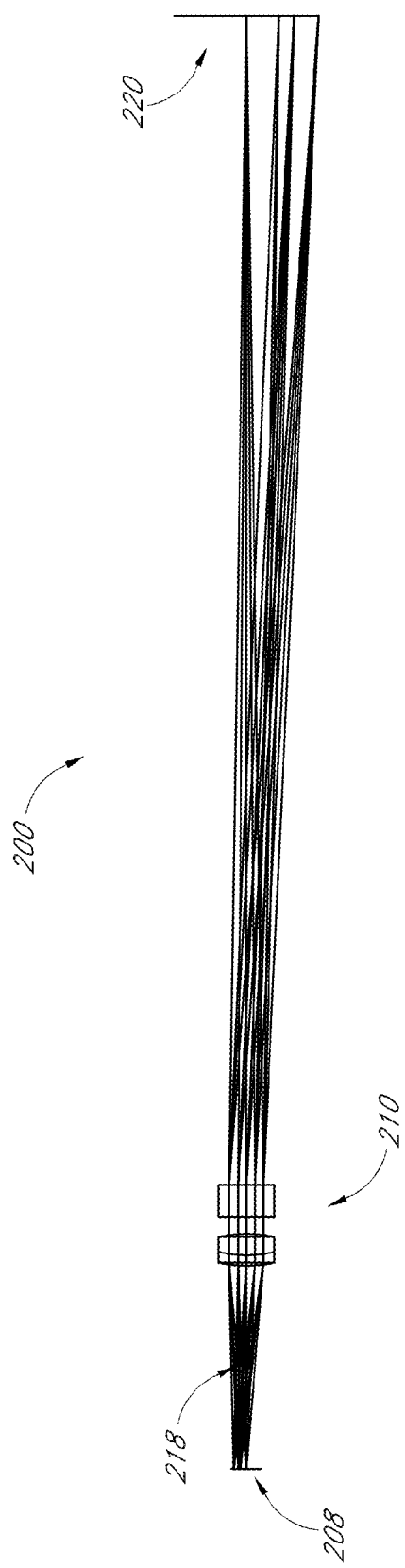
FIG. 3 is a ray trace diagram of the embodiment of the optical angular measurement system of FIG. 1.

As described herein, in some embodiments the imaging lens 210 projects an image of the angular measurement reticle 208 onto the patient's eye. In such embodiments, the focal length of the imaging lens 210 is advantageously set such that the angular measurement reticle 208 and the patient's eye 220 are located at conjugate optical planes. This is illustrated in FIG. 3, which is a ray trace diagram of the embodiment of the optical angular measurement system of FIG. 1. The ray trace diagram illustrates the angular measurement reticle 208 and the imaging lens 210. Light rays 218 from the light source 206 (not shown) that have passed through the reticle 208 are transmitted by the imaging lens 210 to the surface of the patient's eye 220. The ray trace of FIG. 3 is somewhat simplified in that the portion of the patient's eye 220 upon which the image of the reticle 208 is projected (e.g., the cornea) is not actually planar. In practice, the curvature of the eye can be compensated for by providing the image of the reticle 208 formed by the imaging lens 210 with sufficient depth of focus so that the entire image formed on the eye appears acceptably in focus. In other embodiments, it the depth of focus is constrained, the imaging lens 210 may be designed to impart field curvature to the image that approximates the curvature of the patient's eye.

In some embodiments, the focal length of the imaging lens 210, as well as the distance between the imaging lens 210 and the angular measurement reticle 208, is fixed such that the image of the reticle on the eye 220 can only be focused when the optical angular measurement system 200 is positioned at the correct working distance from the patient's eye. In such embodiments, the optical angular measurement system 200 may advantageously include an alignment system for precisely determining the correct working distance between the angular measurement system 200 and the patient's eye 220. One such alignment system is described in US Patent Publication 2009/0103050, entitled "OPTICAL INSTRUMENT ALIGNMENT SYSTEM," the entire contents of which are hereby incorporated by reference herein to be considered a part of this disclosure.

In other embodiments, however, the distance between the imaging lens 210 and the angular measurement reticle 208 is variable, whether by virtue of the imaging lens 210 or the angular measurement reticle 208 being axially adjustable, such that the image of the angular measurement reticle 208 can be projected upon the eye 220 over a range of working distances. For example, in some embodiments, the imaging lens 210 is a zoom lens or otherwise has a variable focal length such that the magnification of the image of the reticle 208 on the eye 220 is variable. The magnification of the imaging lens 220 could be set, whether manually or automatically, such that the image of the angular measurement reticle 208 on the eye 220 is about the size of the patient's pupil, or about the size of the patient's iris, or some other size. Different sized angular measurement images may be best-suited for different surgical procedures.

Figure 4:
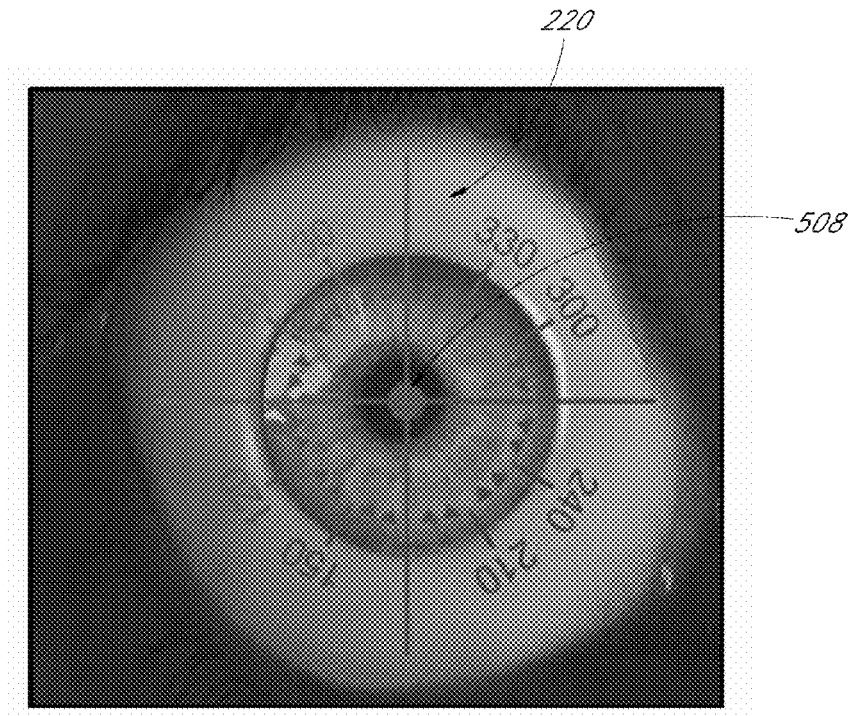
FIG. 4 is a photograph of a patient's eye upon which an embodiment of an angular measurement reticle has been imaged using, for example, the optical angular measurement system of FIG. 1.

FIG. 4 is a photograph of a patient's eye upon which an embodiment of an angular measurement reticle 208 is imaged using, for example, the optical angular measurement system 200 of FIG. 1. FIG. 4 is also representative of a view provided by, for example, a surgical microscope, and upon which an image of an angular measurement reticle is superimposed. The reticle pattern in this embodiment includes a crosshair which may be aligned, for example, with the 0°-180° and 90°-270° horizontal and vertical reference meridians on the patient's eye. This alignment of the crosshair to the horizontal and vertical reference meridians can be accomplished using a rotatable angular measurement reticle 208, or by simply rotating the optical angular measurement system 200 about its optical axis 222. As is evident from the photograph, both the patient's eye and the image of the angular measurement reticle 208 are visible to the surgeon. In some embodiments, the image of the angular measurement reticle 208 is transversely centered on the pupil of the patient's eye, or on the patient's visual axis (which may not necessarily coincide with the center of the pupil). This can be accomplished using an alignment system such as the one described in US Patent Publication 2009/0103050.

Figure 5:
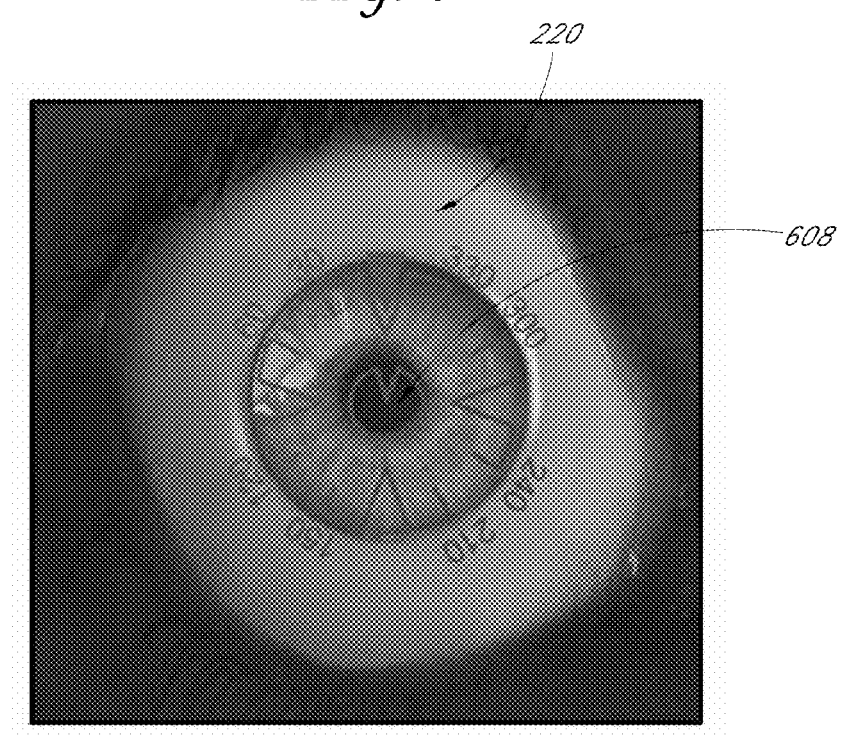
FIG. 5 is a photograph of a patient's eye upon which another embodiment of an angular measurement reticle has been imaged using, for example, the optical angular measurement system of FIG. 1.

FIG. 5 is a second photograph of a patient's eye upon which another embodiment of an angular measurement reticle is imaged using, for example, the optical angular measurement system of FIG. 1. FIG. 5 is likewise also representative of a view provided by, for example, a surgical microscope, and upon which an image of an angular measurement reticle is superimposed. The reticle pattern in FIG. 5 is yet another of the many possible reticle patterns that could be used. This particular pattern includes a central circular shape with an indented wedge. In some embodiments, the wedge is advantageously aligned with either the 0°-180° reference meridian of the eye or the 90°-270° reference meridian.

In some embodiments, the optical angular measurement system 200 is advantageously integrated with another ophthalmic system, such as, for example, a surgical microscope and/or an optical system for measuring the refractive power of a patient's eye, such as a wavefront aberrometer. For example, in some embodiments, the optical angular measurement system 200 is integrated with the surgical microscope/wavefront aberrometer instrument described in US Patent Publications 2005/0243276 and 2005/0241653, both entitled "INTEGRATED SURGICAL MICROSCOPE AND WAVEFRONT SENSOR," the entire contents of both of which are hereby incorporated by reference herein to be considered a part of this disclosure.

Figure 6:
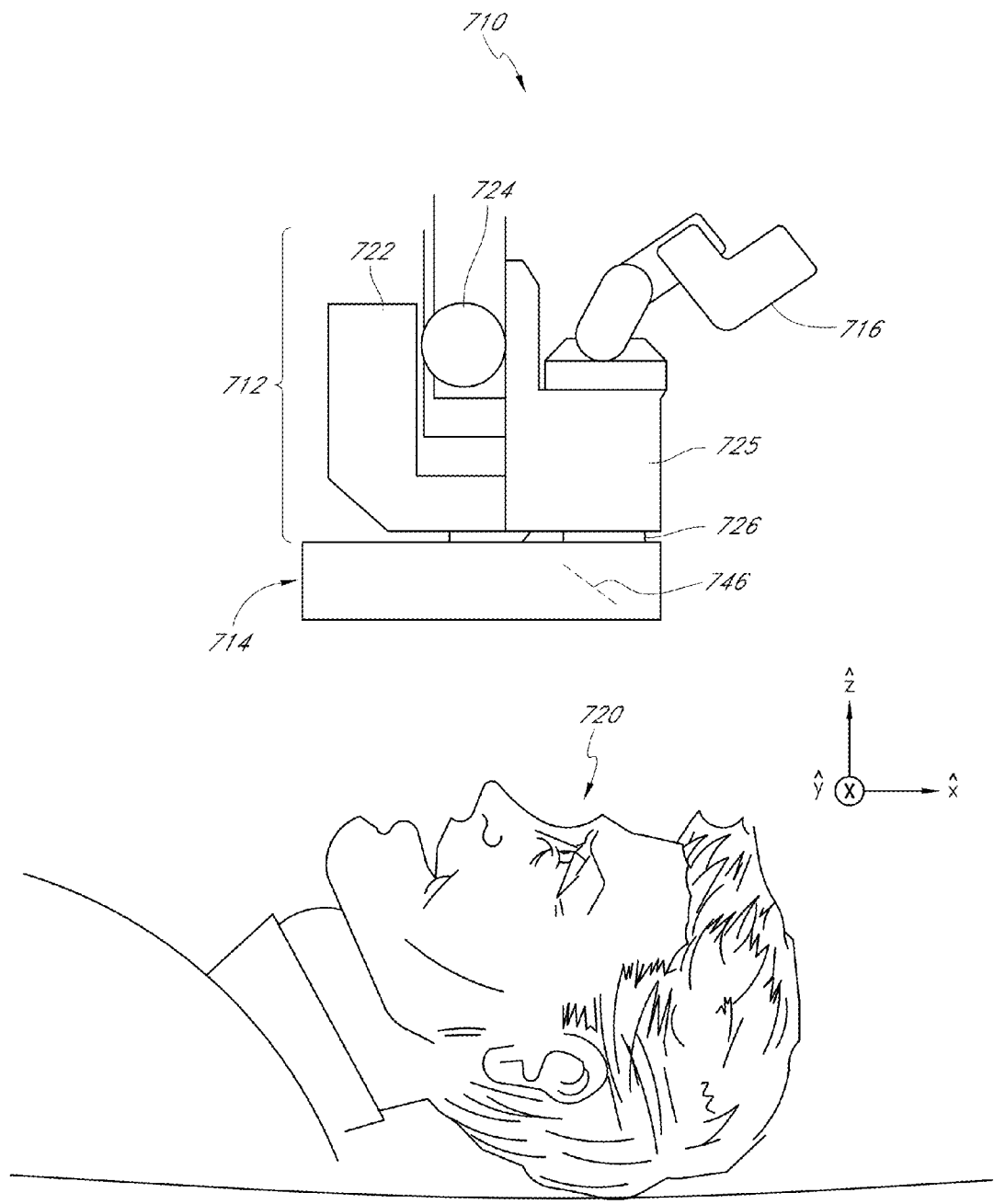
FIG. 6 illustrates an embodiment of an optical instrument that includes a surgical microscope and a wavefront aberrometer, the optical instrument being particularly suited for use by a surgeon during a cataract surgery.

FIG. 6 illustrates an embodiment of an optical instrument that includes a stereoscopic surgical microscope and a wavefront aberrometer, or sensor, the optical instrument being particularly suited for use by a surgeon during a cataract surgery. The optical instrument 710 includes a surgical microscope 712, or other suitable viewing device (e.g., one that provides a three-dimensional view), attached to a wavefront sensor 714, or other optical refractive power measurement device for measuring, for example, the spherical power of a patient's eye and/or the cylindrical power and axis of the eye. In some embodiments, the wavefront aberrometer is mounted onto the surgical microscope such that the angular relationship between the wavefront aberrometer and surgical microscope, for example, about their common optical axis, is known and/or fixed. In some embodiments, this angular relationship is such that, for example, horizontal and vertical lines, or other indicia, of an eyepiece reticle within the surgical microscope are aligned with horizontal and vertical lines, or other indicia, of an angular measurement reticle (e.g., 208) within an optical angular measurement system (e.g., 200) mounted to the wavefront aberrometer, as described herein.

In some embodiments, wavefront aberrometer includes one or more fasteners for removably attaching the wavefront aberrometer to the surgical microscope. In some embodiments the wavefront aberrometer is removably attached to the surgical microscope and a spatial relationship to one another such that the two devices are optically aligned. For example, their respective optical axes are co-linear for at least a portion of their length.

The surgical microscope 712 includes an eyepiece 716, or other viewing mechanism for allowing a doctor to view an eye 720 of a patient. The surgical microscope 712 includes a light source 722 for providing visible light into the optical pathway of the eyepiece 716, a focusing knob 724 for adjusting the focus of the microscope 712, and an objective lens 726, or other suitable lens, for focusing light beams. The surgical microscope may also include a support structure for movably supporting the surgical microscope over a patient in a supine position.

Figure 7:
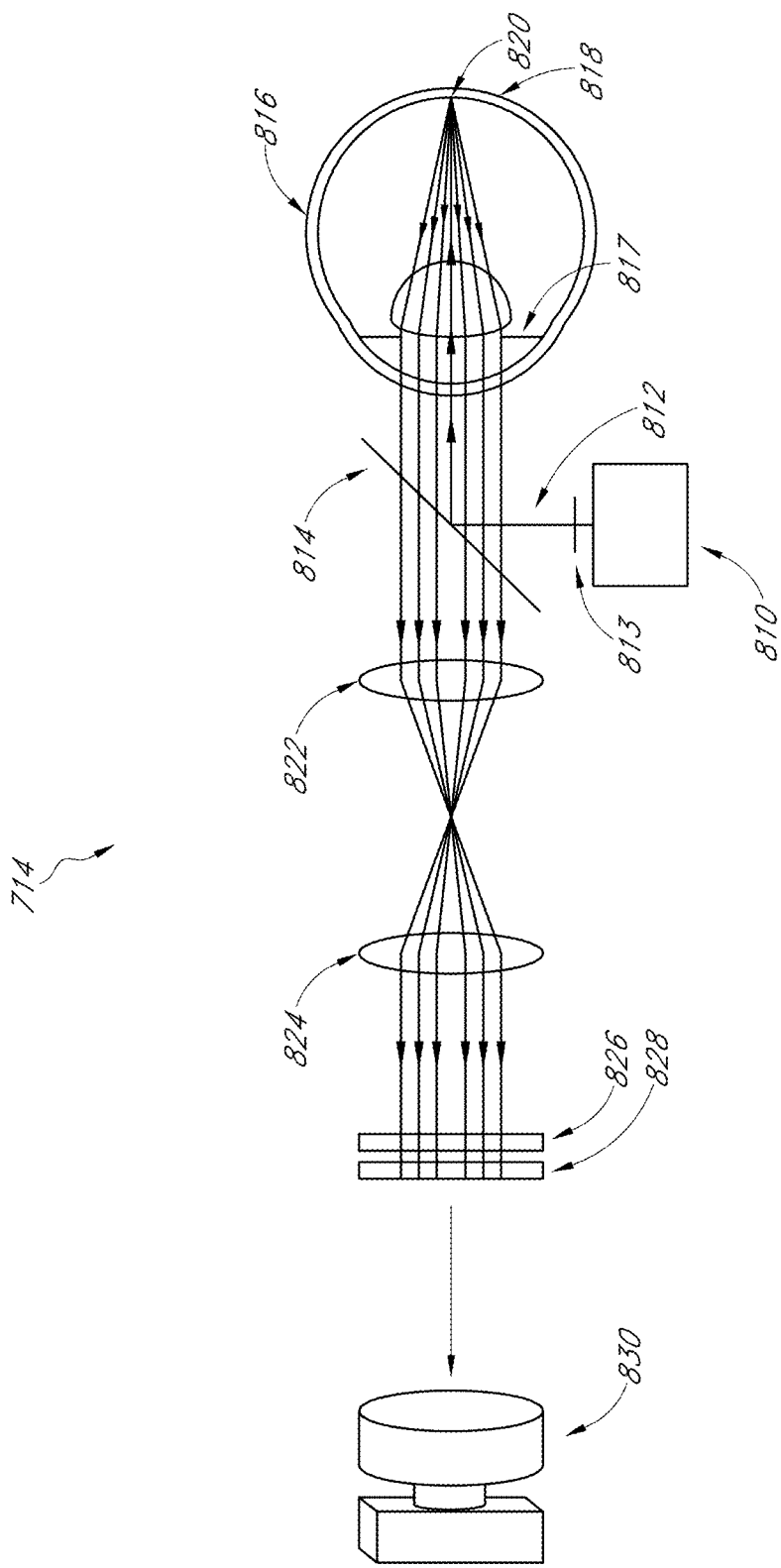
FIG. 7 is an optical schematic of an embodiment of the wavefront aberrometer included with the optical instrument of FIG. 6.

FIG. 7 is an optical schematic of an embodiment of the wavefront aberrometer 714 included with the optical instrument of FIG. 6. The wavefront aberrometer 714 is a Talbot-Moiré wavefront aberrometer and is described in more detail in U.S. Pat. No. 6,736,510, entitled "OPHTHALMIC TALBOT-MOIRÉ WAVEFRONT SENSOR," the entirety of which is hereby incorporated by reference herein to be considered a part of this disclosure. The Talbot-moiré wavefront aberrometer is advantageous in some embodiments because it has a large dynamic range suitable for taking phakic, pseudophakic, and aphakic refractive power measurements of a wide range of individuals. Other types of wavefront aberrometers, other types of instruments for performing refractive power measurements of the eye, can also be used, however. For example, a Shack-Hartmann wavefront aberrometer can be used in some embodiments. In the case of the Talbot-Moiré aberrometer illustrated in FIG. 7, a light source, such as a laser 810 sends a narrow collimated beam of light 812, less than the diameter of the pupil of the eye, usually less than about 1 mm in diameter, to reflect from a beam splitter 814. The beam of light 812 enters the eye 816 through the pupil 817 where it is focused to a point 820 on the retina 818.

The light is reflected from the retina 818 where it passes through a series of relay lenses 822, 824. The light then passes through one or more reticles 826, 828, creating a shadow pattern. A CCD (charge coupled device) camera 830 records the shadow pattern formed by reticles 826, 828. The shadow pattern can be analyzed to determine information regarding the optical aberrations of the patient's eye, including defocus, astigmatic power, and astigmatic axis.

Figure 8:
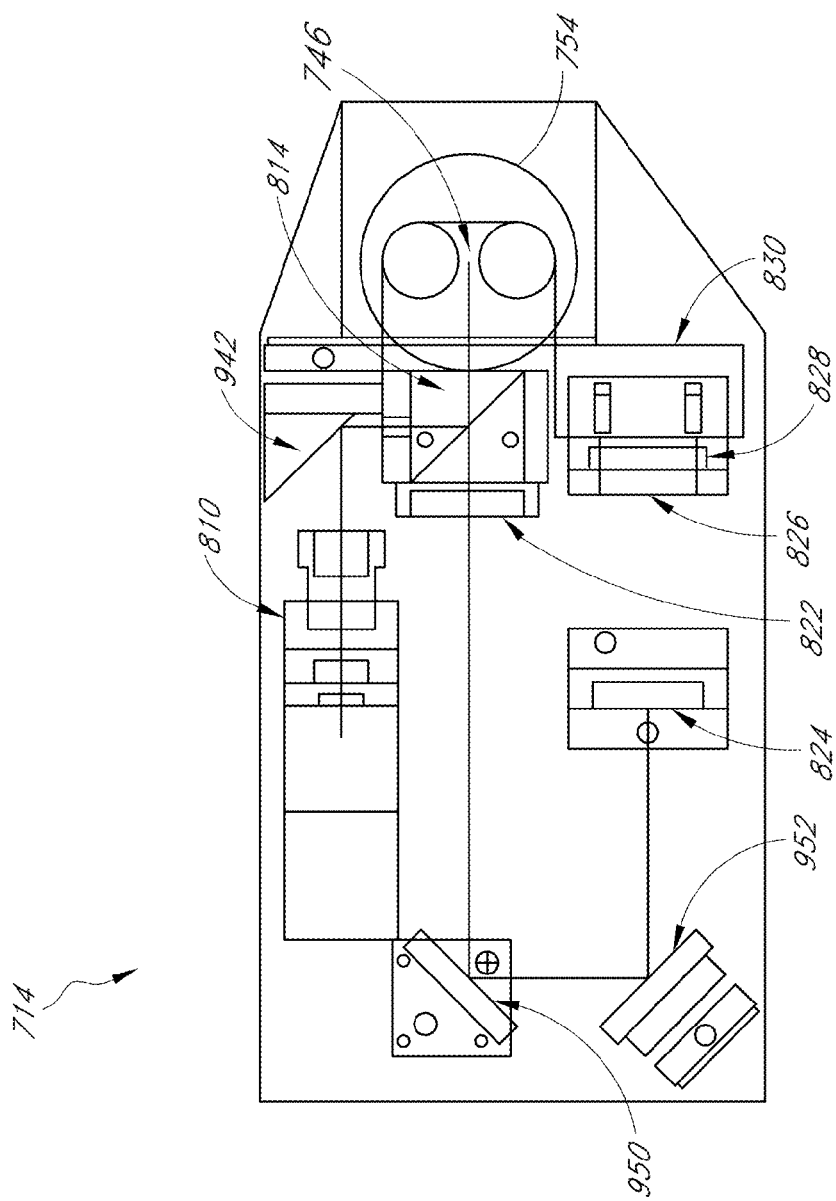
FIG. 8 is a cross-sectional view of an embodiment of the wavefront aberrometer that is schematically illustrated in FIG. 7.

FIG. 8 is a cross-sectional view of the wavefront aberrometer, or sensor, 714 that is schematically illustrated in FIG. 7. In particular, the interior of one embodiment of the wavefront sensor 714 is illustrated. As described herein, the wavefront sensor 714 includes a laser source 810 for creating a beam of light. In some embodiments, the beam of light has a wavelength in the infrared portion of the spectrum. During operation, the beam of infrared light is directed by a mirror 942 toward a beam splitter 814 or other suitable device. An combining optical element, such as a combiner mirror 746 (e.g., a dichroic mirror), a beam-splitter, or other similar device, reflects the beam of infrared light down into the eye of the patient. The combiner mirror 746 preferably reflects the light from the wavefront aberrometer laser 810 while transmitting at least a portion of visible light through an optical passageway that passes through the wavefront aberrometer housing (e.g., the wavefront aberrometer housing may include windows located opposite one another on opposing surfaces to allow visible light to pass through the housing, via, for example, the combiner mirror 746, 2 the surgical microscope) to the surgical microscope so that a surgeon can see the patient's eye while looking through the combiner mirror 746 using the surgical microscope 710.

After the infrared light beam enters the eye, it is reflected, as a wavefront, from the retina of the eye toward the combiner mirror 746. The combiner mirror 746 redirects the light beam through the beam splitter 814 toward the first lens 822. The first lens 822 relays the infrared light beam off of mirrors 950 and 952 toward the second lens 824, which directs the light beam onto the first reticle or grating 826. The light beam is diffracted by the first grating 826 and then travels through the second grating 828, which further diffracts the light beam and creates a final image of the wavefront reflected from the eye, which is captured by the camera 830.

A surgeon 105 can use the surgical microscope 712 to examine the eye 125 of the patient during a surgical procedure. Visible light reflecting from the patient's eye travels along the optical axis of the surgical microscope 712 and the wavefront aberrometer 714 and passes through the combiner mirror 746 into the surgical microscope 712. The wavefront aberrometer 714 and the surgical microscope 712 can allow the surgeon to directly view the patient's eye while the wavefront aberrometer 714 simultaneously performs measurements of the refractive characteristics of the patient's eye. As a result, a surgeon can view the results of a given step of a surgical procedure without having to move the patient, the patient's eye, or the device.

Figure 9:
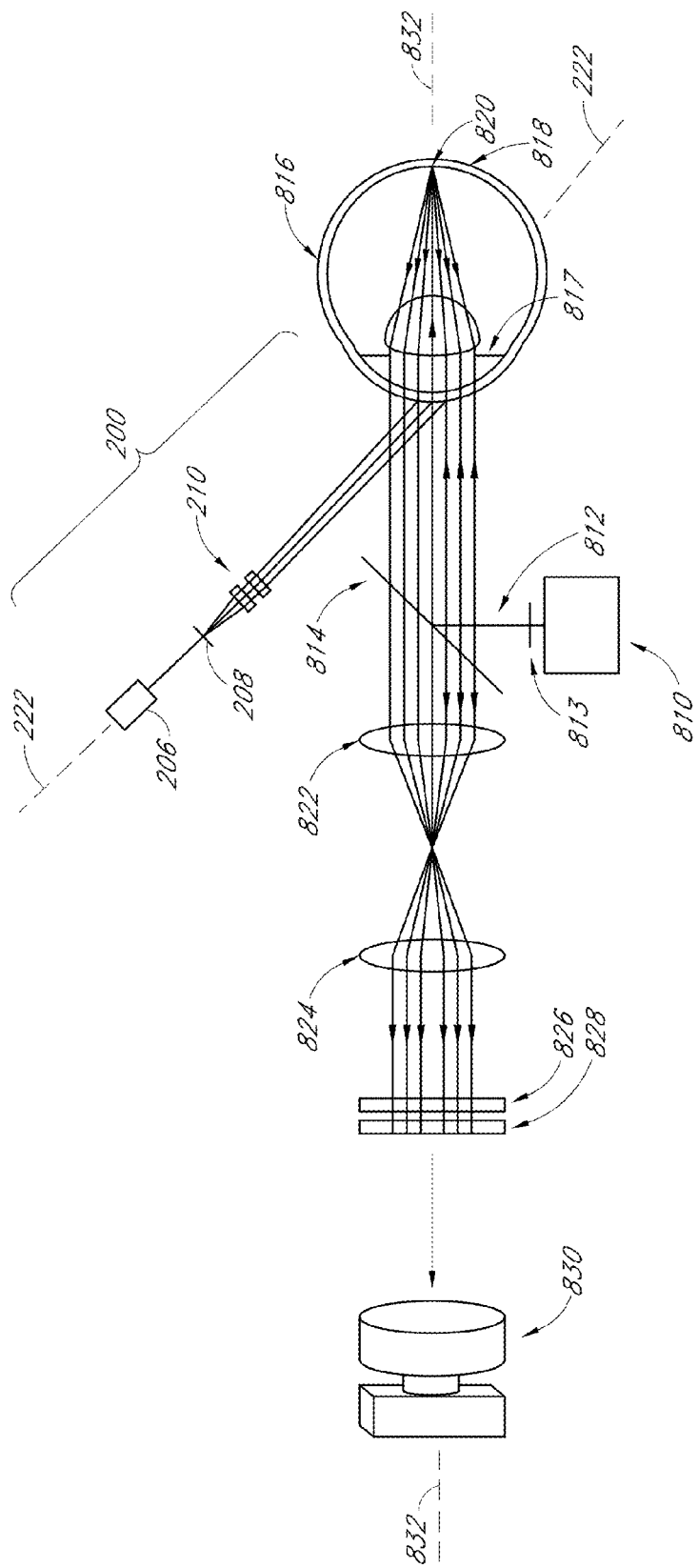
FIG. 9 is an optical schematic of an embodiment of the wavefront aberrometer of FIG. 8 having integrated therewith an optical angular measurement system such as, for example, the one illustrated in FIG. 1.

FIG. 9 is an optical schematic of an embodiment of the wavefront aberrometer 714 of FIG. 7 having integrated therewith an optical angular measurement system such as, for example, the one illustrated in FIG. 1 (e.g., optical angular measurement system 200). The optical schematic of FIG. 9 shows the wavefront aberrometer 714 and its constituent components substantially as shown in FIG. 7. However, the optical angular measurement system 200 is also included. The wavefront aberrometer 714 is aligned with the patient's eye along a first optical axis 832, while the optical angular measurement system 200 is aligned with the patient's eye along a second optical axis 222. In some embodiments, the optical axes 832, 222 are coplanar but are angularly separated and intersect one another in the vicinity of the patient's eye (e.g., at the cornea proximal to its center).

While the optical angular measurement system 200 of FIG. 9 is oriented at an angle with respect to the patient's visual axis (while looking generally straight forward), in some embodiments, the angle is sufficiently small so that the image of the angular measurement reticle 208 that is projected onto the eye is not distorted in a clinically significant way. For example, in some embodiments the optical angular measurement system 200 is oriented at an angle of less than 20°, less than 15°, less than 10°, or less than 5° with respect to the patient's visual axis (while looking generally straight forward) and/or the optical axis 832 of the wavefront aberrometer.

Figure 10:
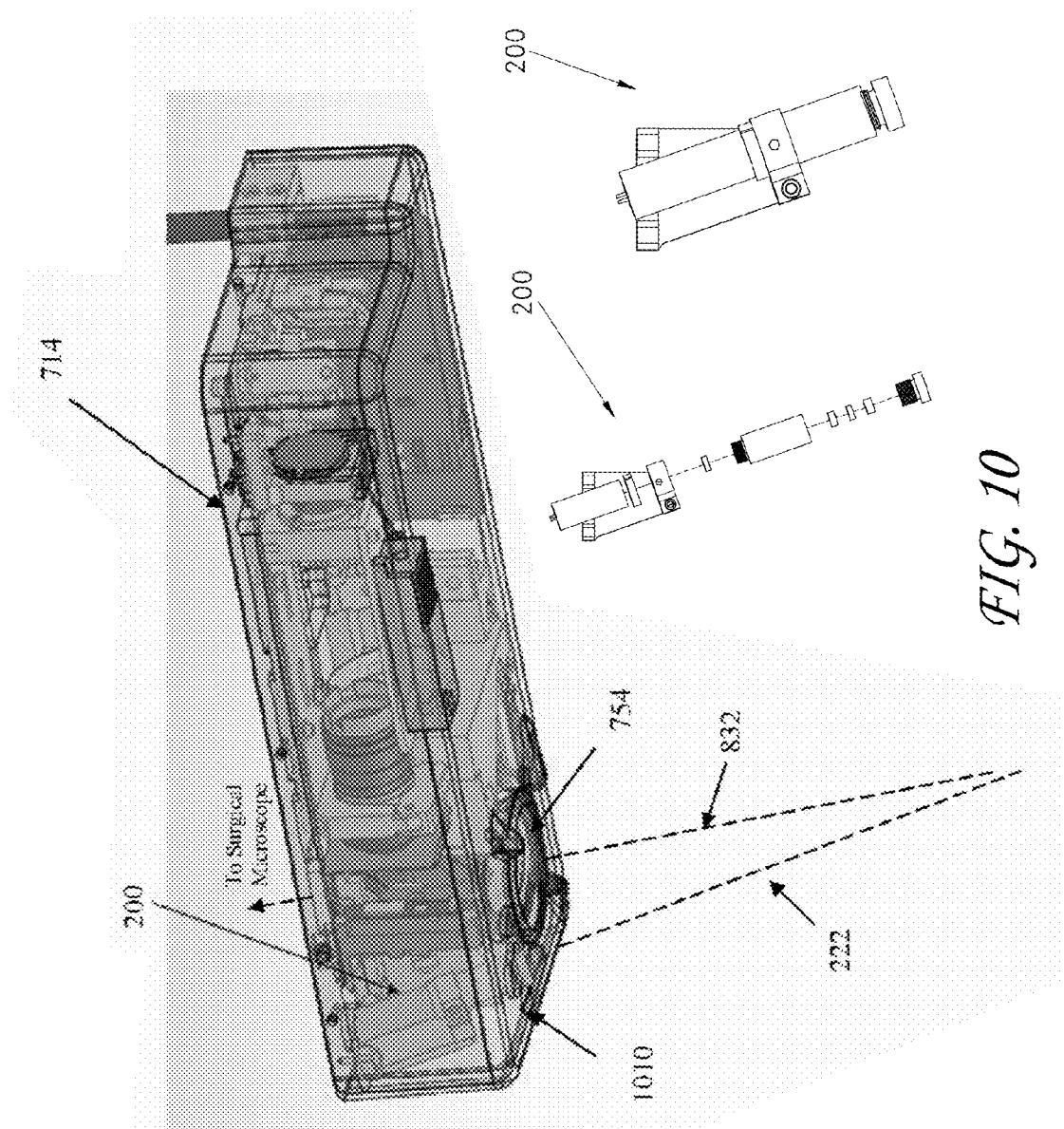
FIG. 10 is a perspective internal view of the wavefront aberrometer with the integrated optical angular measurement system, as schematically illustrated in FIG. 9.

FIG. 10 is a perspective internal view of the wavefront aberrometer 714 with the integrated optical angular measurement system (e.g., 200), as schematically illustrated in FIG. 9. In some embodiments, the optical angular measurement system 200 is mounted within the housing of the wavefront aberrometer 714 using the mounting bracket 214. The mounting bracket 214 can be adapted to provide a desired angle between the optical axes 222, 832 of the optical angular measurement system 200 and wavefront aberrometer 714, respectively, when mounted to a wall or other support structure of the wavefront aberrometer 714. In some embodiments, since the optical angular measurement system 200 is fixedly connected to the wavefront aberrometer 714 (which may in turn be mounted on the surgical microscope 712), the optical angular measurement system 200 can be used to angularly align the wavefront aberrometer 714 and/or the surgical microscope 712 (e.g., about their shared optical axis 832) to a desired angular orientation with respect to the patient's eye. The optical angular measurement system 200 can also be used to angularly align the wavefront aberrometer 714 with the surgical microscope (if, for example, these units are rotatably mounted to one another) by aligning the image of the angular measurement reticle 208 with, for example, a patterned reticle provided in the surgical microscope (e.g., at an internal focal point within the microscope).

In some embodiments, the optical angular measurement system is fixedly mounted with respect to the wavefront aberrometer such that, for example, vertical and horizontal meridian indicia provided by the angular measurement system are aligned with the vertical and horizontal axes of the optical refractive power measurement device. This can be advantageous since it helps to ensure that, for example, a particular cylindrical power axis of a patient's eye measured by the optical refractive power measurement device coincides with the corresponding angle indicated by the angular indicia from the optical angular measurement device. For example, if the optical refractive power measurement device were to measure that a patient's astigmatic axis is located at 37°, then the fixed alignment between the optical refractive power measurement device and the optical angular measurement device would help to ensure that the 37° angle measured by the optical refractive power measurement device coincides with a 37° marking provided by the optical angular measurement device.

In the case of the wavefront aberrometer described herein, in some embodiments, the angular measurement system is fixedly mounted to the wavefront aberrometer such that vertical and horizontal meridian indicia provided by, for example, markings on an angular measurement reticle are aligned with vertical and horizontal axes of a CCD camera that is used to detect optical wavefronts and measure therefrom the cylindrical power and axis of a patient's eye.

Fixed alignment between, for example, the wavefront aberrometer and an optical angular measurement device may be particularly advantageous in the case where the wavefront aberrometer is a removable attachment to a surgical microscope, as described herein. In particular, if the optical angular measurement device were instead fixed to the surgical microscope, then it could be difficult to properly align the angular indicia provided by the optical angular measurement device to the axes of the wavefront aberrometer after repeatedly being attached to, and detached from, the surgical microscope. This could lead to discrepancies between angles measured by the wavefront aberrometer and the corresponding angles indicated by the angular indicia provided by the optical angular measurement device.

The housing and componentry layout of the wavefront aberrometer 714 in FIG. 10 is similar to what is illustrated in FIG. 8. However, whereas the wavefront aberrometer 714 illustrated in FIG. 8 has a single bottom window 754 through which light from the aberrometer 714 and the surgical microscope 712 enters and exits the unit (in addition to a top window facing the surgical microscope), the wavefront aberrometer 714 illustrated in FIG. 10 has an additional bottom window 1010 at which light from the integrated optical angular measurement system 200 exits towards the patient's eye. Also illustrated in FIG. 10 are both the optical axis 222 of the optical angular measurement system 200 and the shared optical axis 832 of the wavefront aberrometer 714 and the surgical microscope 712.

Figure 11:
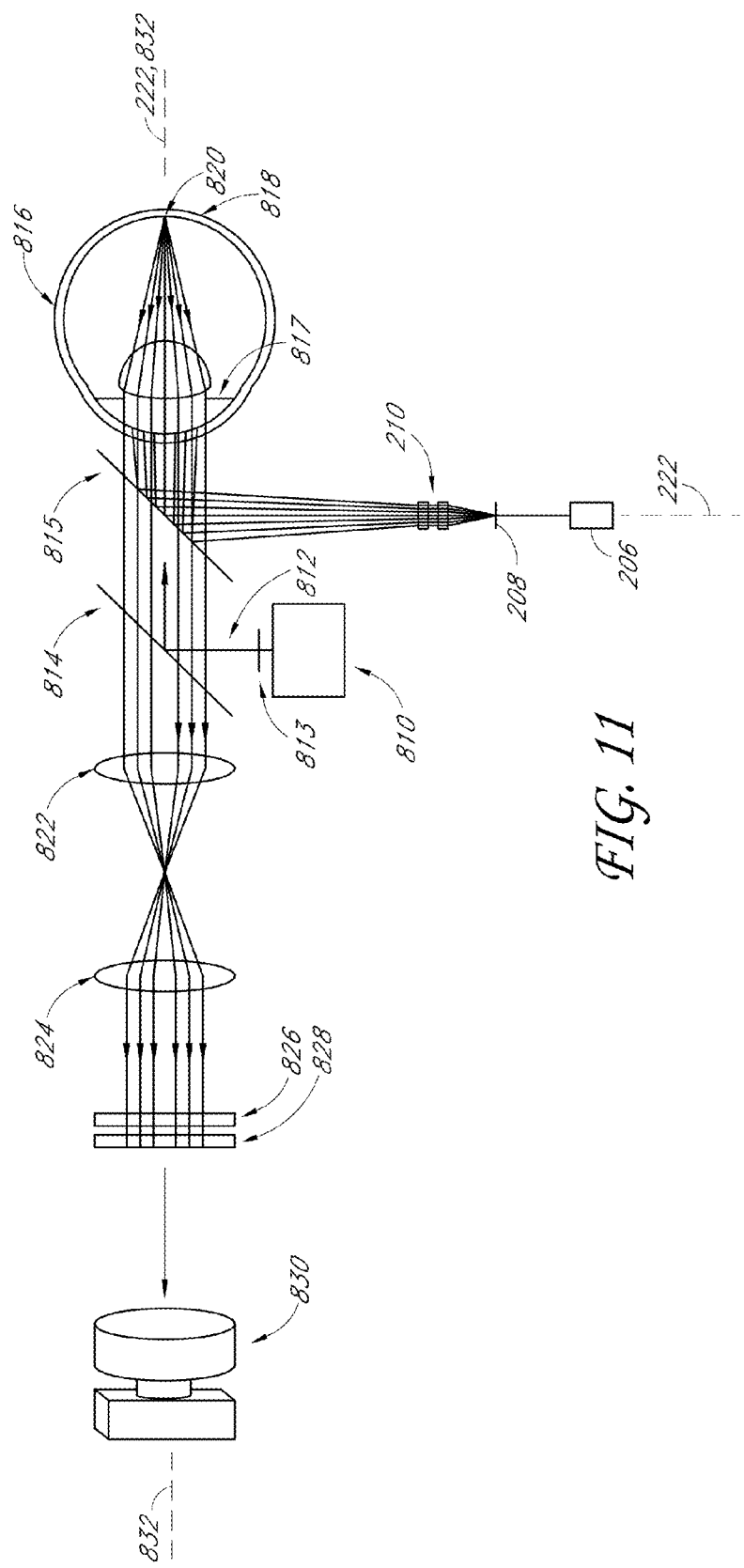
FIG. 11 is an optical schematic of an embodiment of the wavefront aberrometer of FIG. 8 having integrated and optically aligned therewith an optical angular measurement system such as, for example, the one illustrated in FIG. 1.

FIG. 11 is an optical schematic of an embodiment of the wavefront aberrometer of FIG. 7 having integrated and optically aligned therewith an optical angular measurement system such as, for example, the one illustrated in FIG. 1. The optical schematic of FIG. 11 shows the wavefront aberrometer 714 and its constituent components substantially as shown in FIG. 7. However, the optical angular measurement system 200 is also included. In the embodiment of FIG. 11, the optical angular measurement system 200 is optically aligned with the wavefront aberrometer 714 such that both instruments share a common optical axis 222, 832. This can be accomplished by providing a second beam splitter 815 along the optical axis 832 of the wavefront aberrometer 714 to combine light from the imaging lens 210 of the optical angular measurement system 200 with the light from the wavefront aberrometer 714. In this way, the wavefront aberrometer 714, surgical microscope 712, and the optical angular measurement system 200 can be optically aligned with respect to a shared optical axis.

Figure 12:
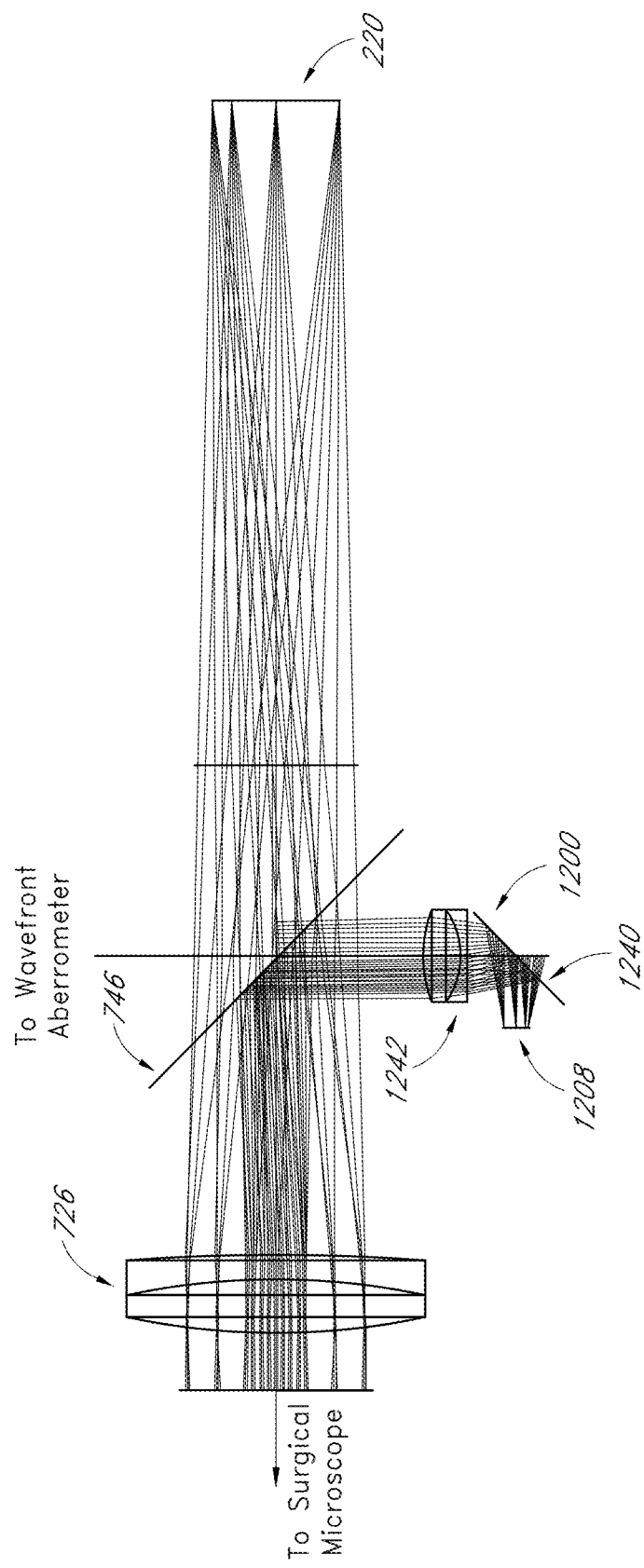
FIG. 12 is a ray trace diagram of an embodiment of an optical angular measurement system for superimposing an image of an angular measurement reticle onto an image of a patients eye that is provided by an ophthalmic instrument such as, for example, the surgical microscope of FIG. 6.

FIG. 12 is a ray trace diagram of an embodiment of an optical system for superimposing an image of an angular measurement reticle onto an image of a patient's eye that is provided by an ophthalmic instrument such as, for example, the surgical microscope of FIG. 6. As described herein, FIG.

1 illustrates an embodiment (200) of the optical angular measurement system that projects an image of an angular measurement reticle 208 onto the patient's eye. The projected image of the angular measurement reticle 208 in such embodiments is visible to the surgeon both when viewing the patient's eye through the surgical microscope 212 and with the naked eye independent of the surgical microscope or other optical instruments. In contrast, FIG. 12 illustrates an embodiment (1200) of the optical angular measurement system in which an image of the angular measurement reticle is instead superimposed upon the image of the patient's eye that is provided by the surgical microscope 712, though it could alternatively be superimposed on an image from some other type of instrument (e.g., the reticle image can be superimposed by computer software on a camera image of the patient's eye, in this or other embodiments). In such embodiments, the image of the angular measurement reticle is only visible to the surgeon when viewing the patient's eye through the surgical microscope 712. Many of the features that have been disclosed with respect to the projection embodiment (e.g., 200) of the optical angular measurement system can be equally applied to or used with the superimposition embodiment (e.g., 1200) of the optical angular measurement system.

The optical angular measurement system 1200 includes a light source (not shown) that illuminates an angular measurement reticle 1208, for example, in a manner similar to what has been described with respect to the optical angular measurement system 200 illustrated in FIG. 1. The angular measurement reticle 1208 is likewise similar to what has been described with respect to the optical angular measurement system 200 of FIG. 1. The optical angular measurement system 1200 may additionally include an optional mirror 1240 that can be used to fold the optical path of the optical angular measurement system 1200 into a more compact space, as well as an optional lens 1242 for adjusting the apparent distance of the angular measurement reticle 1208 from the surgical microscope 712.

In some embodiments, the optical angular measurement system 1200 is fixedly mounted relative to a surgical viewing device such as, for example, the surgical microscope 712 at a position where light from the optical angular measurement system 1200 can be combined with the optical path of the surgical viewing device using a combining optical element, such as a beam splitter, dichroic combiner mirror, etc. For example, in some embodiments, the optical angular measurement system 1200 is mounted on the opposite side of the combiner mirror 746 from the wavefront aberrometer 714.

In some embodiments, the combiner mirror 746 is adapted so that it is reflective to the light used by the optical angular measurement system 1200 while still transmitting at least a portion of visible light from the eye to the surgical microscope. Thus, light from the optical angular measurement system 1200 that is incident upon the combiner mirror 746 is reflected toward the objective lens 726 of the surgical microscope 712. This can be accomplished by, for example, forming an optical layer on the combiner mirror 746 to act as a spectral notch reflector over the wavelength band of light used by the optical angular measurement system 1200. In some embodiments, the width of the spectral notch is made small enough to avoid appreciably interfering with the image provided to the surgeon by the surgical microscope. In some embodiments, the optical angular measurement system 1200 is configured to operate at a wavelength, or range of wavelengths, such as long red wavelengths, though other wavelengths are also possible. It should be appreciated that there are also other ways of configuring the combiner mirror 746 to reflect light used by the optical angular measurement system while still transmitting sufficient visible light to the surgical microscope from the eye to provide an accurate image of the eye. Alternatively, other architectures can be used where optical pathways from the surgical microscope and the optical angular measurement system are combined using multiple combiner optical elements.

In some embodiments, the surgical microscope and the optical angular measurement system 1200 are configured such that the surgical microscope images the angular measurement reticle 1208 while simultaneously imaging the patient's eye. For example, the angular measurement reticle 1208 can be located at an object plane (e.g., a plane that is conjugate to the image plane of the microscope) of the surgical microscope.

In some embodiments, the angular measurement reticle 1208 is positioned the same optical path distance away from the objective lens 726 of the surgical microscope as the patient's eye 220. In such embodiments, the optional lens 1242 of the optical angular measurement system 1200 can be foregone since the angular measurement reticle 1208 and the patient's eye 220 will both be simultaneously focused by the surgical microscope 712, for example, when the instrument is located at its intended working distance from the patient's eye.

In some embodiments, however, it may be beneficial to set the angular measurement reticle 1208 at a different optical path distance from the objective lens 726 of the surgical microscope than a patient's eye 220. For example, in some embodiments, it may be desirable to make the optical angular measurement system 1200 more compact by shortening this distance. In other embodiments, a longer path distance may be desirable. However, in either case a lens 1242 can be provided along the optical path of the system 1200 between the angular measurement reticle 1208 and the objective lens 726 of the surgical microscope to adjust the apparent distance between the objective lens 726 of the surgical microscope and the angular measurement reticle 1208 to match the actual distance between the objective lens 726 and the patient's eye 220, for example, when the instrument is located at the intended vertical working distance above the patient's eye. In this way, the angular measurement reticle 1208 and the patient's eye at 220 can both be simultaneously imaged by the surgical microscope despite differences in the optical path length from the objective lens 726 to each of these planes.

In some embodiments, the apparent distance between the angular measurement reticle 1208 and the surgical microscope is variable by way of, for example, a zoom lens or axial movement of the reticle. In this way, the instrument can operate at a variety of working distances while the surgical microscope still clearly images the angular measurement reticle.

Figure 13:
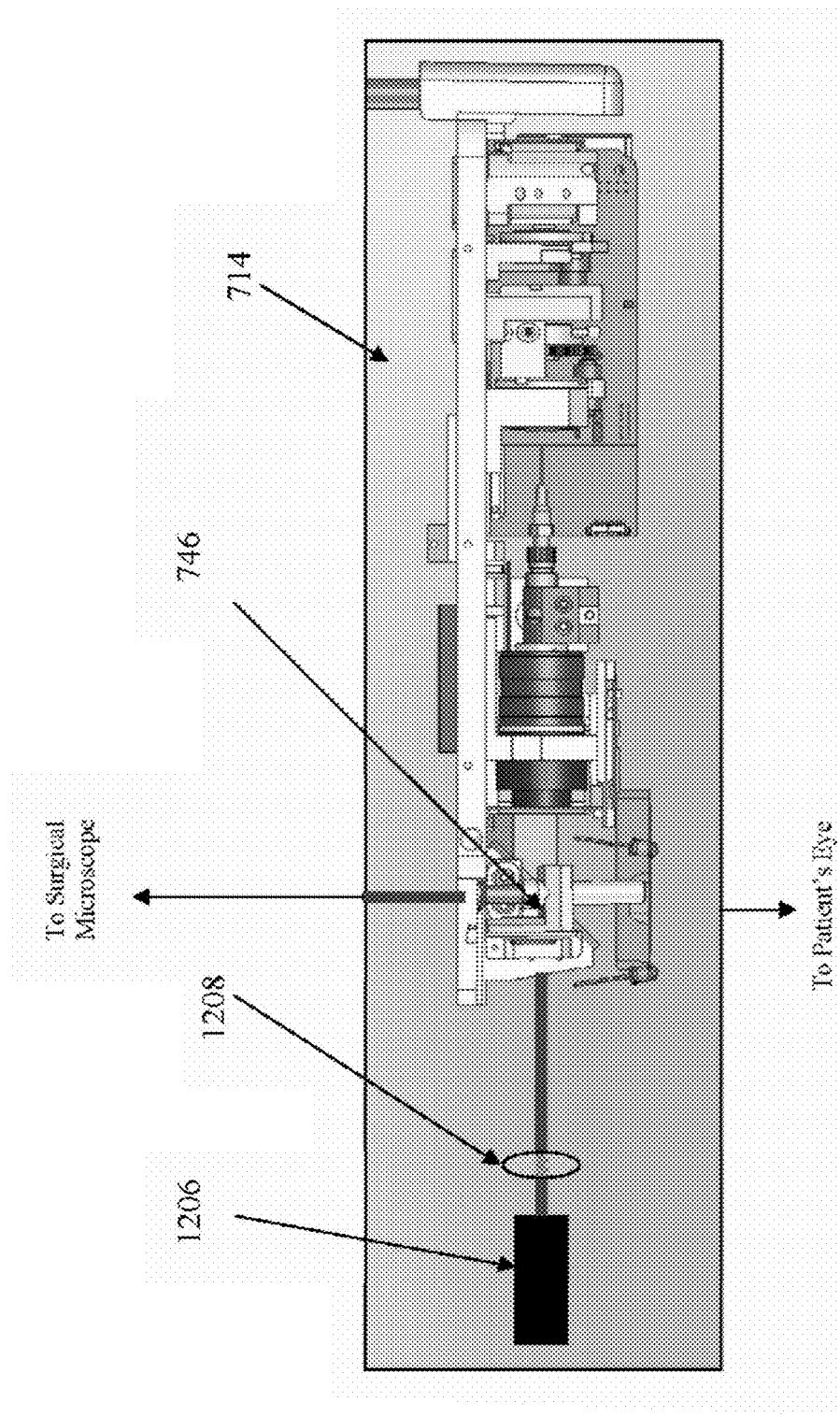
FIG. 13 is an internal side view of an embodiment of the wavefront aberrometer of FIG. 7 having integrated and optically aligned therewith an optical angular measurement system such as, for example, the one illustrated in FIG. 12.

FIG. 13 is an internal side view of an embodiment of the wavefront aberrometer of FIG. 7 having integrated and optically aligned therewith an optical reticle superposition system such as, for example, the one illustrated in FIG. 12. The optical angular measurement system 1200 is illustrated on the left-hand side of the combiner mirror 746, while the wavefront aberrometer 714 is illustrated on the right-hand side of the combiner mirror. The light source 1206 of the optical angular measurement system 1200 illuminates the angular measurement reticle 1208. The light is transmitted via the reticle 1208 is incident upon the combiner mirror 746, which directs the light into the surgical microscope 712.

In some embodiments, an optical angular measurement device can be a laser line projector that can be integrated and optically aligned with, for example, a wavefront aberrometer, or other refractive measurement device, that is mounted on the surgical microscope. Such a laser line can serve as one type of alignment indicator for showing, for example, the angular axis to which the astigmatic axis of a toric IOL should be aligned, as described herein The laser line projector may include a laser source that is aligned with, for example, the optical axis that is shared by the wavefront aberrometer and the surgical microscope. This can be done using a beam splitter or other combining optical element to combine a visible laser beam from the laser source with the light from the wavefront aberrometer and/or the surgical microscope. The laser source can be incident upon, for example, a rotating mirror located, for example, between the laser source and the beam splitter. This rotating mirror can be rotatable about the optical axis of the instrument, and about an axis that is orthogonal to the optical axis of the instrument. Rotation of the mirror about the axis that is orthogonal to the optical axis of the instrument at a high speed can create the appearance of a laser line that is projected onto the patient's eye.

The mirror can be rotated about the optical axis of the instrument in order to specify the orientation of the projected laser line. This can be done, for example, manually by the surgeon based on angular gradations marked on the laser line projector, or automatically using a stepper motor or other actuator based on a signal from the computer indicating the appropriate amount and direction of rotation of the toric IOL. In some embodiments, the orientation of the laser line projector is determined based on an angle and direction of rotation relative to the orientation of the instrument at the time the total refractive measurement of the pseudophakic eye is taken. The mirror can be rotated about the optical axis of the instrument to an orientation that coincides with, for example, the axis to which the toric IOL should be aligned (i.e., the calculated astigmatic axis of the cornea). This visible indicia allows the surgeon to easily and conveniently view the calculated astigmatic axis of the cornea while viewing the toric IOL through the surgical microscope.

In some embodiments, the indicia of the axis to which the toric IOL should be aligned is determined by a rotatable reticle that is projected onto the eye or viewable by the surgeon through the surgical microscope. For example, in the case of the wavefront aberrometer mounted to a surgical microscope, as described herein, the light from the wavefront aberrometer and the surgical microscope can be combined using a beam splitter. In some embodiments, a reticle is positioned on the side of this beam splitter opposite from the wavefront aberrometer. Thus, the beam splitter can be used to pass light reflecting off of the reticle, or transmitted through the reticle, to the surgical microscope so that the reticle is viewable by the surgeon through the surgical microscope. For example, the reticle may appear superimposed upon the image viewed through the microscope. Other arrangements for achieving this effect are also possible.

The reticle can, for example, be positioned at a distance from the beam splitter that is substantially equal to the intended working distance between the beam splitter and the corneal apex of the patient's eye so that the reticle can be viewed through the surgical microscope in focus. The reticle can include a mark to indicate the intended axis of alignment for the toric IOL (i.e., the calculated axis of corneal astigmatism). The reticle can also be rotatable so as to properly orient the mark on the reticle at the astigmatic axis of the cornea. The reticle can be, for example, manually rotatable based on angular gradations provided on the reticle housing, or automatically rotatable by a motor or other actuator based on a signal from the computer indicating the appropriate amount and direction of rotation of the toric IOL. In some embodiments, the orientation of the laser line projector is determined based on an angle and direction of rotation relative to the orientation of the instrument at the time the total refractive measurement of the pseudophakic eye is taken. In some embodiments, an optical angular measurement device, an optical refractive power measurement device (e.g., a wavefront aberrometer), and/or a surgical microscope are communicatively coupled to a computer. In some embodiments, the computer can be used to process measurement data from the optical refractive power measurement device (e.g., wavefront data) in order to determine, for example, the spherical power of the patient's eye and/or the cylindrical power and axis. Based on these measurements, for example, the computer can determine (e.g., calculate) an alignment value. Alternatively, or in addition, the alignment value could be provided by the surgeon via a user interface.

The alignment value can indicate the angular orientation to which the astigmatic axis of a toric IOL should be aligned. This can be determined, for example, from pseudophakic and/or aphakic measurements of the refractive power of the patient's eye intra operatively during, for example, a cataract surgery, as described herein. The alignment value could also indicate a desired angular orientation of some other type of ocular implant. In addition, the alignment value can indicate the angular location where some surgical action should be performed, such as an incision (e.g., a phaco incision or a limbal relaxing incision).

The computer can then control the optical angular measurement device to adjust some aspect of the angular indicia based on the alignment value. For example, the computer could control the angular orientation of an alignment indicator. The alignment indicator could be a marking on an angular measurement reticle, a laser line, or other mark, projected onto the eye, etc. Other types of alignment indicators can also be used. In this way, the computer can provide an automated indication to a surgeon of a particular angular orientation to be used during the surgical procedure. Other aspects of the angular indicia, in addition to the angular orientation of an alignment indicator, can also be controlled based on input from another optical device, such as a wavefront aberrometer, or user input. These include, for example, the shape, size, pattern, design, information content, etc. of the angular indicia.

In some embodiments, the angular indicia provided by an optical angular measurement device can be made switchable between "on" and "off" states, while still allowing substantially full operation of the surgical microscope and/or optical refractive power measurement device. The on/off state of the angular indicia can be controlled based on user input through a user interface, or automatically based on input from another device. This can be advantageous by allowing angular indicia to be switched on when it is needed to make an angular measurement or to perform an angular alignment, for example, while allowing the angular indicia to be switched off when it is not needed, when it may be distracting to the surgeon, or when it would interfere with the operation of, for example, the optical refractive power measurement device or the surgical microscope.

The angular indicia provided by optical angular measurement devices described herein can be made switchable between on and off states by, for example, configuring the respective light sources used by the optical angular measurement devices to be switchable on and off. Alternatively, or in addition, a controllable shutter can be used to controllably block or pass light from an optical angular measurement device, thereby effectively switching the angular indicia off or on. For example, with reference to the embodiment illustrated in FIG. 10, a controllable shutter could be placed over the window 1010 or at an appropriate position within the lens tube 216 in order to prevent an image of the angular measurement reticle from being projected onto the patient's eye. With respect to the embodiment illustrated in FIG. 12, a controllable shutter could be placed in a position, for example, at a position before the combiner mirror 746 in order to prevent light from the optical angular measurement device from being transmitted to the surgical microscope. This is in contrast to an angular measurement reticle provided within a surgical microscope (e.g., within an ocular, etc. of the surgical microscope), which generally cannot be disabled without also disabling the surgical microscope itself even though angular indicia may not always be necessary and, in fact, may even be distracting in certain circumstances. Thus, in some embodiments, it is advantageous that the surgical microscope and the optical angular measurement device, despite being optically aligned, have non-fully-overlapping optical pathways, that allow the angular indicia to be selectively disabled without disabling the surgical microscope, as described herein. In some embodiments, it is likewise advantageous that the wavefront aberrometer, or other optical refractive power measurement device, and the angular measurement device, despite being optically aligned, each has an optical pathway, at least a portion of which is not shared by the other. Other techniques for configuring an optical angular measurement device to be switchable on and off can also be used.

Positioning of a Toric Intraocular Lens

In some embodiments, in order to select and properly align a toric IOL to a desired angular axis so as to correct the cylindrical refractive power of the cornea of a patient's eye during cataract surgery, the axis and magnitude of the cylindrical power of the cornea are first determined. Since the crystalline lens is to be removed during the cataract surgery, it is desirable to obtain measurements of the spherical and cylindrical refractive power that are attributable solely to the cornea. Refractive measurements obtained by certain other instruments that measure the total refractive power of the eye while the natural lens is intact may include contributions to the refractive power that are attributable to the natural crystalline lens. Thus, these types of instruments may not be ideally suited for measurements where only the refractive power attributable to the cornea is sought.

Measurements of the refractive power of the cornea are typically obtained using an instrument such as a keratometer or corneal topographer. Such instruments measure the curvature of the corneal topographer directly or indirectly. Keratometric data generally includes K values that represent the refractive power of the cornea in orthogonal meridians that pass through the corneal apex, or anatomical center, of the cornea. These values, K1 and K2, can be expressed in terms of the radii of curvature or as the dioptric power of the cornea along these orthogonal meridians.

The keratometric data may comprise the magnitude of the spherical refractive power of the cornea, as well as the magnitude and axis of the cylindrical refractive power of the cornea. The axis of the cylindrical refractive power can be measured as an angle from a reference meridian on the cornea. For example, the reference meridian may be the 0°-180° horizontal meridian. Once the axis of the cylindrical refractive power of the cornea is known, a toric IOL implant can be aligned with respect to the axis so as to correct the astigmatism of the cornea. For example, the toric IOL may include an amount of negative refractive power to compensate for the meridian of the cornea with the greatest amount of positive refractive power. In such cases, the toric IOL is properly aligned when the most negative meridian of the toric IOL coincides with the most positive meridian of the patient's cornea.

In a typical cataract surgery, the surgeon obtains pre-operative keratometric data to determine the magnitude of the spherical and cylindrical refractive power of the patient's cornea, as well as the axis of the cylindrical power. The accuracy of the keratometric measurement of the axis of the cylindrical refractive power of the cornea has certain limitations. For example, keratometric measurements are typically made with respect to the corneal apex. However, in general, the visual axis of the patient's eye is not centered on the corneal apex. Thus, the magnitude and axis of the cylindrical refractive power actually experienced by the patient, as measured through the pupil, can be different from the magnitude and axis of the keratometric cylindrical power that is measured with respect to the corneal apex. This difference between the magnitude and axis of cylinder measured using a keratometer and the values measured by refraction through the pupil can result in sub-optimal corrective outcomes for cataract surgery patients.

After obtaining pre-operative keratometric data from the patient's cornea, the surgeon also determines the position at which he or she will make the phaco incision near the limbus of the cornea. The phaco incision, typically made at 0° or 180° is a small incision through which the surgeon removes the patient's natural lens and inserts an IOL implant. The phaco incision itself induces an amount of cylindrical refractive power in the cornea. Since keratometric data is generally obtained pre-operatively, this data does not measure the induced cylinder that later results from the phaco incision. The magnitude of induced cylinder from the phaco incision generally varies from patient to patient. It depends on such factors as age and gender of the patient, as well as patient-specific properties of the eye. (Its axis generally coincides with the location of the phaco incision.) It is difficult to accurately predict the amount of induced cylindrical refractive power for any given patient. For one patient, a 2.6 mm phaco incision could induce 0.25 D of cylinder, while for another it could induce 0.75 D of cylinder. In both cases, however, the induced cylindrical refractive power may be assumed to be equal to the 0.5 D average amount of induced cylinder, or some other predicted value. Any error between the predicted and actual values of the magnitude of induced cylinder can result in sub-optimal corrective outcomes for cataract surgery patients.

A toric lens calculator can be used to calculate an estimate of the correct magnitude of cylinder for a toric IOL implant. The toric lens calculator also outputs an estimate of the correct axis of orientation of the toric IOL so as to properly correct the patient's corneal astigmatism. The inputs to the toric lens calculator may include the keratometric measurements of the patient's cornea, including the measured magnitude and axis of corneal astigmatism, the predicted magnitude of induced cylinder from the phaco incision, and the angular location of the phaco incision. The toric lens calculator calculates the magnitude of cylinder of an IOL implant that will correct the patient's corneal astigmatism. The toric lens calculator also calculates the proper axis of orientation for the toric IOL. This information may be obtained using crossed cylinder calculations.

Such calculations compute the cumulative magnitude and axis of cylindrical refractive power that results from two or more separate cylinder components, each having its own magnitude and axis. For example, in the case of cataract surgery where a toric IOL will be used, the magnitude and axis of cylinder of the cornea are measured. The magnitude and axis of induced cylinder resulting from the phaco incision are predicted. These two cylinder components are then combined using the crossed cylinder equation to obtain an estimate of the total magnitude and axis of cylinder that will be displayed by the cornea after the phaco incision has been made.

The general process for using crossed cylinder calculations to combine the measured keratometric cylinder with the estimated induced cylinder is as follows:

Convert cylinder values from polar coordinates to Cartesian coordinates:

Keratometric Corneal Cylinder=Magnitude (Cyl$_C$) and Axis (A$_C$)

$X_C = Cyl_C * Cos(2*A_C)$ $Y_C = Cyl_C * Sin(2*A_C)$

Induced Cylinder=Estimated Magnitude (Cy and Phaco Incision Axis (A$_I$)

$X_I = Cyl_I * Cos(2*A_I)$ $Y_I = Cyl_I * Sin(2*A_I)$

The Crossed Cylinder is obtained by adding the Cartesian coordinates:

$X_N = (X_C + X_I)$ $Y_N = (Y_C + Y_I)$

The Cartesian coordinates of the new cylinder are converted back to polar coordinates as follows:

$Cyl_N = Square\ Root((X_N)^2 + (Y_N)^2)$ $A_N = Arctan((Y_N)/(X_N))/2$

If $X_N > 0$ and $Y_N > 0$ then, $A_N = A_N$

If $X_N < 0$, then $A_N = A_N + 90$

If $X_N > 0$ and $Y_N < 0$, then $A_N = A_N + 180$

A toric IOL is selected for the patient based on the output of the toric lens calculator. For example, if a patient's cornea is predicted to have +2.5 D of cylinder after the phaco incision has been made, then a toric IOL with less than or equal to −2.5 D of cylinder can be selected to correct or reduce the patient's astigmatism. For example, a toric IOL with a magnitude of astigmatic power as close to, but not greater than, −2.5 D can be selected. If a toric lens having exactly the amount of cylinder necessary to correct the corneal cylinder were to be obtained, and if it were to be inserted into the patient's eye at exactly the axis of the corneal cylinder, then the corneal astigmatism of the patient's eye could in theory be perfectly corrected. However, since toric IOLs are typically only manufactured with a finite number of discrete cylinder power values, it may not be possible to choose one that perfectly cancels the astigmatism of the patient's cornea. If a toric IOL having exactly the magnitude of cylinder necessary to correct the cylinder of the patient's cornea is available, then it is referred to as a fully-correcting IOL. If the magnitude of the cylinder of the toric IOL does not exactly correspond to the magnitude of cylinder of the patient's cornea, then the toric IOL is referred to as a non-fully-correcting IOL.

In most cases, a fully-correcting toric IOL is not available. If the magnitude of the toric IOL does not perfectly correspond to the magnitude of the cornea's cylindrical refractive power, then the patient's eye will exhibit a certain amount of residual astigmatism even after the cataract surgery has been performed. Even if a fully-correcting IOL is available, there may be some degree of error in the angular positioning of the toric lens. This misalignment of the IOL also results in residual astigmatism even if the toric IOL is theoretically fully-correcting. Misalignment of a toric IOL can also exacerbate the residual astigmatism in the case of a non-fully-correcting toric IOL.

The theoretical residual astigmatism of a fully-correcting toric IOL is, of course, 0.0 D. However, this correction is only obtained if the toric IOL is properly aligned to the axis of the cornea's cylinder. The residual astigmatism of a non-fully-correcting toric IOL that is properly aligned with the corneal cylinder is the difference between the magnitude of cylinder of the cornea and that of the toric IOL. The residual astigmatism of a non-fully-correcting toric IOL will be greater than this baseline value if the toric IOL is misaligned.

In the past, most residual astigmatism attributable to non-optimal alignment of the toric IOL could be traced to post-surgical rotation of the IOL. However, now that improved IOLs are available which generally do not rotate after the surgery, residual astigmatism is more attributable to misalignment of the toric lens during the cataract surgery. While some of this surgical misalignment may be caused by surgical techniques, it can also be attributable to error in the axis calculated by the toric lens calculator. In other words, even if it were possible to always precisely orient the IOL implant at the axis determined by the toric lens calculator, misalignment of the lens would still occur due to errors in the calculated value. As described above, these errors can result from, for example, the fact that the magnitude of induced astigmatism is unknown and from the fact that keratometric data is measured with respect to the corneal apex rather than the visual axis of the patient.

Even small amounts of misalignment of the toric IOL with respect to the axis of cylinder of the patient's cornea can result in clinically significant increases in the theoretically-attainable residual astigmatism in any given case. This is illustrated by FIGS. 14 and 15.

Figure 14:
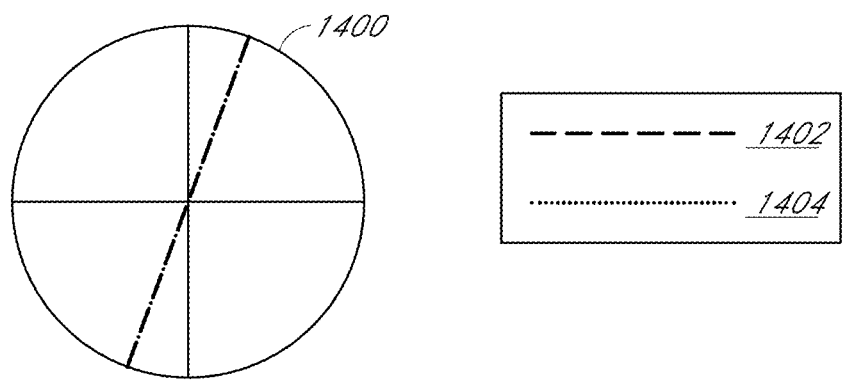
FIG. 14 is a schematic plan view of a patient's cornea illustrating the proper alignment of a toric IOL.

FIG. 14 is a schematic plan view of a patient's cornea 1400. Suppose that the illustrated cornea 1400 has +2.5 D of cylindrical refractive power at 80°, as illustrated by the dashed line 1402. Dotted line 1404 represents the orientation of a toric IOL implanted within the patient's eye. Suppose that the toric IOL is a non-fully-correcting IOL with −2.06 D of cylinder. If the axis of the toric IOL is positioned at 80°, as illustrated in FIG. 14, then the resulting residual astigmatism is 0.44 D at 80°.

Figure 15:
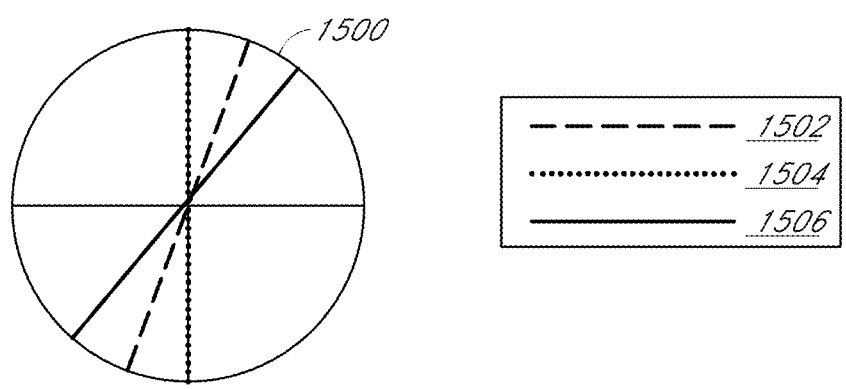
FIG. 15 is a schematic plan view of a patient's cornea illustrating the placement of a misaligned toric IOL.

FIG. 15 illustrates the scenario of a misaligned toric IOL. FIG. 15 is a schematic plan view of a patient's cornea 1500. Suppose that's the cornea 1500 yet again has +2.5 D of cylinder at 80°. This is illustrated by dashed line 1502. Suppose further that the same −2.06 D toric IOL is inserted into the patient's eye, but instead of being oriented at 80°, the toric IOL is oriented 10° counterclockwise at 90°, as represented by dotted line 1504. The residual astigmatism in such a scenario is no longer +0.44 D. Instead, it is +0.90 D. In addition, one might suppose that the axis of the residual astigmatism would be located between 80° and 90°. However, the axis of the residual astigmatism would actually be measured at 54°, as represented by solid line 1506.

If the surgeon were to measure the angular orientation of the toric IOL postoperatively using a slitlamp microscope, he or she would note that the axis of the residual astigmatism is 36° clockwise from the actual orientation of the IOL. As illustrated, a misalignment of the toric IOL by 10° results in a much larger error in the axis of the residual astigmatism. The misalignment of the toric IOL also results in a greater magnitude of residual astigmatism than the theoretical optimal value that would have been obtained if the toric IOL had been properly oriented.

FIG. 16 is a table 1600 that illustrates the impact of misalignment of a toric IOL on the residual astigmatism for patients having several different prescriptions. The first prescription in the table 1600 corresponds to the one just described with respect to FIGS. 14 and 15. It is a patient with −1.00 D of sphere and +2.50 D of cylinder at 80°. A non-fully-correcting toric IOL with −2.06 D of cylinder is used for this patient. The table 1600 illustrates the magnitude and axis of residual astigmatism for cases where the toric IOL is aligned at 100°, 90°, 85°, 80°, 75°, 70°, 60°, respectively. The values of the residual astigmatism are given in the "Refraction Measurement" column. Note that a misalignment of only 5° from the 80° axis of corneal cylinder results in the axis of the residual astigmatism being 19° off from the axis of corneal cylinder. Larger misalignments can result in even larger departures from the theoretical axis of residual astigmatism using a given toric IOL. The "Refraction Measurement" column also includes the measured value of sphere. It can be seen from the table that misalignment of the toric IOL not only affects the residual astigmatism (magnitude and axis of cylinder) but also the magnitude of spherical refractive power.

Table 1600 also includes example data using the following prescriptions: −0.50+2.00×45°, −0.50+2.00×110°, −1.00+0.60×75°, and −0.75+4.00×90°. The values in the "Refraction Measurement" column of the table 1600 can be calculated using the crossed cylinder equation if the magnitude and axis of both the corneal astigmatism and the toric IOL are known. The columns titled "Recommended Rotation" and "Measurement Axis Versus Lens Axis" will be described below.

After the surgeon has determined the proper refractive power and orientation of the tonic IOL implant, as described above, he or she may proceed with the cataract surgery. With the patient in an upright position, for example, at a slitlamp microscope, the surgeon may use a horizontal bubble level to indicate the 0°-180 meridian of the cornea. The surgeon can align a device with angular gradations or graduation marks, such as a Mendez gauge, to the eye. Then, using the Mendez gauge, the surgeon may mark the limbus of the eye at the angular axis calculated by the toric IOL calculator. This can be done at the slitlamp or later during the surgery. The surgeon will later use this mark to align the toric IOL to the estimated axis of the corneal astigmatism once the patient is relocated to a supine surgical position. In some embodiments, the marking of the axis for alignment of the toric IOL, or for the horizontal or vertical meridian, is done while the patient is in an upright position because the keratometric data used to calculate the estimated axis of the corneal astigmatism after the phaco incision is also typically measured while the patient is in an upright position. If the tonic IOL axis were marked with the patient in supine position without reference to an axis of the eye marked while the patient was in the upright position, a clinically significant amount of error could be introduced due to cyclotorsion of the eye during the transition from the upright to the supine position.

Once an alignment axis, or other reference axis, for the toric IOL is marked, the patient is placed in a supine surgical position. The surgeon makes the phaco incision and removes the natural crystalline lens, for example, by phacoemulsification. Once the natural lens is removed, the surgeon may fill the capsular bag with visco-elastic material in order to maintain the form of the capsular bag, and to ease rotation of the toric IOL within the bag. The surgeon then inserts the toric IOL and aligns its axis using the previously-made mark on the limbus. The visco-elastic material is then aspirated from the capsular bag.

In some cases, it can be expected that this aspiration process will cause the IOL to rotate somewhat. Some toric IOLs are designed to rotate easily in one direction while resisting rotation in the opposite direction. For example, some IOLs are configured such that the easy direction of rotation is clockwise. Thus, a surgeon may initially misalign the toric IOL by a few degrees (i.e., typically less than 10°) counter-clockwise from the mark on the limbus in anticipation that the toric IOL will rotate somewhat clockwise during aspiration of the visco-elastic material. Once the visco-elastic material has been aspirated, the surgeon may perform any necessary additional clockwise rotation of the toric IOL until it is aligned with the mark on the limbus.

The amount of initial misalignment of the toric IOL to account for possible rotation during aspiration is typically done in the direction opposite from the direction in which the IOL rotates easily. Thus, any rotation of the IOL during aspiration, which will occur in the direction of easy rotation, will tend to rotate the IOL toward its final position of alignment. If inadvertent rotation of the IOL during aspiration is expected, the rotation in the direction opposite from the direction of easy rotation should be more than the maximum expected amount of inadvertent rotation. This helps to avoid the necessity of having to later rotate the toric IOL against the easy direction of rotation to its final alignment position. However, the initial misalignment to compensate for rotation during aspiration should not exceed 10° in order to limit the amount of necessary rotation of the toric IOL after the visco-elastic material has been removed.

It is often the case in cataract surgeries that the residual astigmatism after the surgery is not as low as theoretically anticipated. In fact, it has been found during testing of a sample size of 33 cases that the residual astigmatism in 27% of toric lens outcomes was greater than 0.75 D from the theoretically-expected result. As previously mentioned, two possible causes of these sub-optimal outcomes are as follows: 1) the magnitude and axis of cylinder of the toric IOL are calculated from keratometric data, which is measured from the corneal apex rather than the center of the pupil; and 2) the keratometric data does not take into account the induced astigmatism that results from the phaco incision; instead, the induced astigmatism is estimated, usually based upon the average amount of induced astigmatism across a number of patients.

Each of the foregoing factors can result in the toric IOL being improperly aligned with the axis of the cylindrical refractive power of the patient's cornea. It is this misalignment that results in sub-optimal residual astigmatism. As illustrated by FIG. 16, even small amounts of alignment error can result in clinically significant increases ire the residual astigmatism. Thus, it would be beneficial to reduce the impact of the two foregoing factors in order to improve patient outcomes.

Surgical outcomes could be improved with accurate intraoperative knowledge of the magnitude and axis of cylindrical refractive power of the cornea that is to be corrected by the toric IOL. The magnitude and axis of the cylinder of the cornea can be accurately calculated postoperatively, however. This is done by measuring the total residual astigmatism of the eye postoperatively (i.e., after the eye has healed) and solving the crossed cylinder equation to yield the magnitude and axis of the corneal cylinder, which was unknown at the time of the surgery.

As discussed above, the crossed cylinder equation can be used to calculate an estimate of the residual astigmatism that will result after implantation of a toric IOL. This estimate is based on an estimate of the magnitude and axis of cylinder attributable solely to the cornea as well as knowledge of the magnitude and axis of the implanted toric IOL. The accuracy of the estimated residual astigmatism is limited by the accuracy of the estimate of corneal astigmatism. However, if the residual astigmatism is measured postoperatively using, for example, a wavefront aberrometer, the crossed cylinder equations can be solved to determine what the magnitude and axis of corneal astigmatism actually must have been. Once the true magnitude and axis of corneal astigmatism are known, the crossed cylinder equations can be used to calculate the actual optimal orientation of the toric IOL. If the surgeon deems it worthwhile, a second surgery could be performed to position the toric IOL at this optimal orientation. However, this approach is limited by the requirement for multiple surgeries as well as the fact that the phaco incision made during the second surgery could once again alter the magnitude and axis of the corneal astigmatism, leading once more to sub-optimal orientation of the toric IOL.

This problem can be solved with the capability to accurately measure the true magnitude and axis of the corneal cylinder intra-operatively after the phaco incision has been made. This can be done, for example, using a wavefront aberrometer mounted to, and optically aligned with, a surgical microscope used by the surgeon to perform the cataract surgery. Such a device is described in co-pending U.S. patent application Ser. Nos. 11/110,653 and 11/110,968, both filed Apr. 20, 2005 and entitled "INTEGRATED SURGICAL MICROSCOPE AND WAVEFRONT SENSOR." One type of wavefront aberrometer that is suitable for performing the types of intra-operative measurements described herein is a Talbot-Moiré wavefront aberrometer such as the ones described in U.S. Pat. No. 5,963,300, issued Oct. 5, 1999 and entitled "OCULAR BIOMETER," and in U.S. Pat. No. 6,736,510, issued May 18, 2004 and entitled "OPHTHALMIC TALBOT-MOIRÉ WAVEFRONT SENSOR." An alignment system for accurately positioning a wavefront aberrometer to perform intra-operative measurements during cataract surgery is described in co-pending U.S. patent application Ser. No. 12/206,974, filed on Sep. 9, 2008 and entitled "OPTICAL INSTRUMENT ALIGNMENT SYSTEM." The entire contents of each of the foregoing references are hereby incorporated by reference herein to be considered part of this disclosure.

Figure 17:
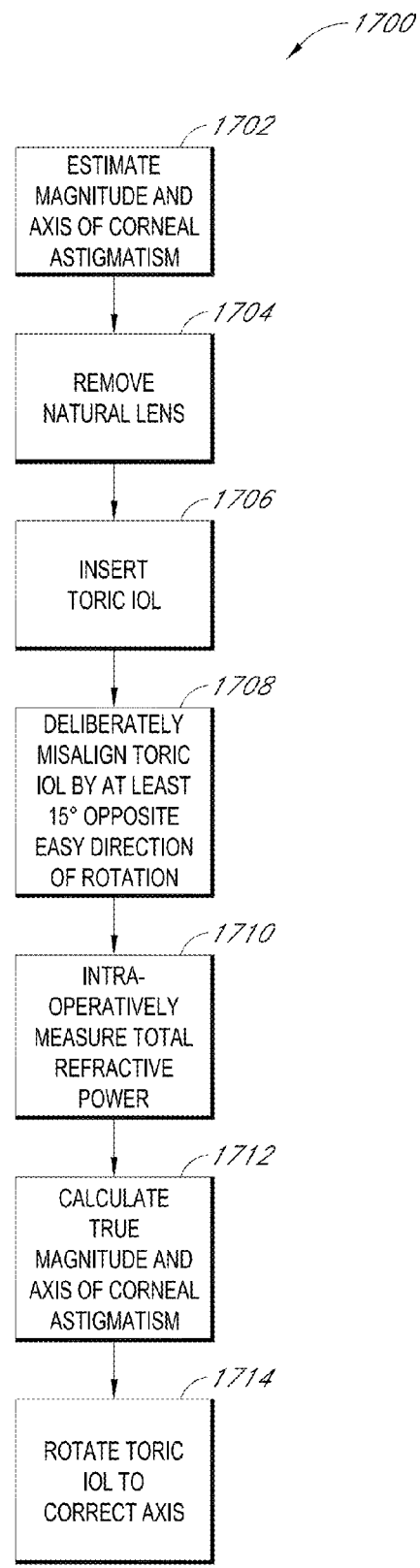
FIG. 17 is a flow chart illustrating a method for more accurately positioning a toric IOL during cataract surgery based on an intraoperative pseudophakic measurement.

FIG. 17 illustrates a method 1700 for performing a cataract surgery in a manner that results in more accurate alignment of a toric IOL to the axis of the patient's corneal astigmatism, thus reducing residual astigmatism and improving the patient's surgical outcome. At block 1702, the surgeon obtains an estimate of the magnitude and axis of the patient's corneal astigmatism. This estimate can be obtained, for example, using a keratometer or corneal topographer to obtain keratometric data. In some embodiments, the keratometric data is measured while the patient is in an upright position. As previously discussed, the keratometric data comprises the measured magnitude and axis of the patient's corneal astigmatism.

In some embodiments, the surgeon may try to improve this keratometric estimate of the cylindrical refractive power of the patient's cornea by estimating the amount of induced astigmatism that will later result from the phaco incision. For example, crossed cylinder calculations can be performed to determine how the estimated induced astigmatism will affect the measured keratometric axis of the patient's corneal astigmatism. Nevertheless, in some embodiments, the initial orientation of the tonic IOL when inserted in the patient's eye according to the method 1700 need not be as accurate as in conventional techniques. This is described more fully below. Thus, in some embodiments, it is not necessary to determine the effect of the estimated induced astigmatism on the measured keratometric axis of the patient's corneal astigmatism, and such calculations can be omitted.

Once the estimate of the magnitude and axis of the patient's corneal astigmatism is obtained at block 1702 (whether this estimate is based solely on keratometric data, or on both keratometric data and an estimate of induced astigmatism), the surgeon may proceed to mark the position of the axis estimate on the limbus of the patient's eye. Once more, however, in some embodiments the initial orientation of the toric IOL according to the method 1700 can have a lower degree of accuracy than may be required when using conventional techniques. Thus, while a surgeon performing a cataract surgery according to method 1700 may choose to mark the position of the estimated axis of corneal cylinder, in some embodiments such marking is not required and can be foregone. In some embodiments, any cyclotorsion of the eye that occurs when the patient is placed in the supine position may not be clinically significant in view of the lax accuracy requirements of the initial orientation of the toric IOL according to method 1700, as described more fully below. Skipping the marking of the limbus with the estimated axis of corneal cylinder can allow for the cataract surgery to be performed more quickly. The surgery may also be performed more cost-effectively since tools that may have been required to make such a mark may no longer be required.

At block 1704 of method 1700, the surgeon removes the natural lens from the patient's eye. At block 1706, the surgeon inserts a toric IOL into the patient's eye. These steps may involve the introduction of visco-elastic material to the capsular bag, as in conventional techniques. The actual toric IOL that is used in any given surgery can be selected, for example, based on the pre-operative keratometric estimate of the magnitude of the patient's corneal astigmatism.

At block 1708, the surgeon deliberately misaligns the axis of the toric IOL by at least 15° from the estimated axis of corneal cylinder. In some embodiments, the misalignment is in the direction opposite from the direction of easy rotation of the toric IOL. In other embodiments, the surgeon deliberately misaligns the axis of the tonic IOL by at least 30° in the direction opposite from the direction of easy rotation of the toric IOL. This deliberate misalignment allows the surgeon to later rotate the tonic IOL in the direction of easy rotation to obtain the correct alignment, as discussed herein. For example, many toric IOLs are manufactured so as to easily rotate in a clockwise direction. Thus, in some embodiments, the surgeon deliberately misaligns the axis of the tort IOL by at least 15° counterclockwise from the estimated axis of corneal cylinder, while in other embodiments the amount of deliberate misalignment is at least 30° counterclockwise. In the case of a toric IOL that has no preferential direction of rotation, the deliberate misalignment of the toric IOL can be in either direction from the estimated axis of corneal astigmatism.

In some embodiments, the amount of deliberate misalignment is counterclockwise by at least 15° but no more than 20°. In some embodiments, the amount of deliberate misalignment is counterclockwise by at least 20° but no more than 25°. In some embodiments, the amount of deliberate misalignment is counterclockwise by at least 25° but no more than 30°. In some embodiments, the amount of deliberate misalignment is counterclockwise by at least 30° but no more than 35°.

In some embodiments, the amount of deliberate misalignment is counterclockwise by at least 35° but no more than 40°. In some embodiments, the amount of deliberate misalignment is counterclockwise by at least 40° but no more than 45°. In some embodiments the amount of deliberate misalignment is at least 30°. In some embodiments the amount of deliberate misalignment is counterclockwise by at least 30° but no more than approximately 90°. It will be understood by those of skill in the art that the deliberate misalignment will be clockwise from the estimated axis of corneal astigmatism for IOLs having a counterclockwise direction of easy rotation.

Once the toric IOL has been inserted into the capsular bag and deliberately misaligned with respect to the estimated axis of corneal astigmatism, at block 1710, the total refractive power of the patient's pseudophakic eye (i.e., the eye after implantation of the IOL) is intra-operatively measured while the patient remains in the supine surgical position. In some embodiments, this intra-operative measurement is performed using, for example, a Talbot-Moiré wavefront aberrometer mounted on a surgical microscope, though other systems that measure the refractive properties of the eye could be used (e.g., one incorporating a Shack-Hartmann wavefront aberrometer).

In some embodiments, the visco-elastic material is aspirated from the capsular bag prior to the intra-operative measurement of total refractive power of the eye so as to reduce any effect that the visco-elastic material may have on the measurement. For example, the visco-elastic material may cause the toric IOL to be tilted somewhat in the capsular bag such that there is a non-zero angle between the optical axis of the IOL and the patient's visual axis. This tilt could impact the measurement of total refractive power by introducing a tilt component to an intra-operative wavefront measurement. The visco-elastic material could also introduce other first, second, or higher-order artifacts into the wavefront measurement. In other embodiments, however, the visco-elastic material is left in place during the measurement of total refractive power of the eye so as to later facilitate rotation of the toric IOL so that its astigmatic axis is aligned to that of the patient's cornea.

The measurement of the total refractive power of the patient's eye includes sphere and cylinder components from both the toric IOL and the patient's cornea. Crossed cylinder calculations can be performed to determine the actual magnitude and axis of unknown corneal astigmatism that, when combined with the known magnitude and axis (which can be measured, for example, using the devices described herein) of cylinder of the toric IOL, resulted in the measured composite magnitude and axis of total refractive astigmatism of the cornea/IOL system measured intra-operatively using, for example, a wavefront sensor.

Combining measured cylinder with toric lens cylinder:
Convert cylinder values from polar coordinates to Cartesian coordinates using the above equations to yield $X_M, Y_M, X_L$ & $Y_L$ Calculate "true" corneal cylinder magnitude and axis:

$X_{TC} = (X_M - X_L)$ $Y_{TC} = (Y_M - Y_L)$

Convert to polar coordinates using the equations above.
Required toric lens rotation (described further below) is equal to $A_L - A_{TC}$ This calculation can be performed using a computer, whether general-purpose or specialized, a scientific calculator, or some other computing device. The computer may be communicatively coupled with a wavefront sensor used to perform the intra-operative refractive measurements. The computer may comprise a processor, a memory module, and a user interface. In some embodiments, the processor is programmed to calculate the actual magnitude and axis of corneal astigmatism based on input information comprising the intra-operatively measured magnitude and axis of total refractive cylinder and the known magnitude and axis of cylinder of the toric IOL. The processor may, store for example, the calculated actual magnitude and axis of corneal astigmatism in the memory module. In addition, the processor may output the actual corneal astigmatism values to the surgeon using the user interface. The user interface may also allow for the surgeon to input information such as, for example, the keratometric measurements of a patient's eye, the model, sphere, and cylinder of a selected toric IOL, etc. In some embodiments, the user interface provides the surgeon with prompts that help to guide the surgery.

In some embodiments, the computer is communicatively coupled to a repository of information (e.g., a central database) by, for example, a computer network (e.g., the internet). The repository of information may include information about available IOLs to help the surgeon make a selection of a suitable IOL for use in a patient's surgery. The computer may also upload information comprising the measurements of a patient's aphakic, or pseudophakic, eye to the repository of information. This information can be collected and made available for analysis, for example, by other surgeons or researchers. In some embodiments, the collection of aphakic or pseudophakic measurements made by a particular surgeon can be analyzed to determine surgeon-specific corrective factors that can be applied to improve that surgeon's results in the future. For example, if a particular surgeon has a demonstrated tendency, based on the collected measurements, to achieve outcomes that are 0.5 D worse than the theoretically-achievable result, than appropriate corrections can be made for that surgeon's future patients with regard to toric IOL selection, calculation of corneal cylinder, etc.

With reference to FIG. 16, the foregoing calculation is used to determine the information in the "Corneal Refraction" column, which is unknown, from the information in the "Toric Lens Power and Axis" column and the "Refraction Measurement" column. FIG. 16 also includes a "Recommended Rotation" column and a "Measurement Axis Versus Lens Axis" column. The "Measurement Axis Versus Lens Axis" column contains angles that are representative of the difference between the axis of actual measured total refraction and the axis of orientation of the toric IOL. The "Recommended Rotation" column includes angles which represent the amount of angular rotation which should be imparted to the toric IOL in order to properly align it with the axis of corneal cylinder that is determined using the foregoing calculation. In some embodiments, the processor that calculates the actual magnitude and axis of corneal astigmatism can also be used to calculate the amount by which the toric IOL should be rotated to achieve proper orientation for correcting the corneal astigmatism. This value can be outputted to the surgeon by way of the user interface. In some embodiments, this recommended rotation value typically has a magnitude in the range of the amount of deliberate initial misalignment ±10°. The recommended rotation will typically be in the direction opposite from the direction of initial misalignment (e.g., clockwise). The ±10° may be due to any error in the initial estimate of the astigmatic axis of the cornea.

The intra-operative measurements of total refractive power do not suffer from the same defects as the pre-operative keratometric measurements and induced astigmatism estimates described herein. Namely, the total refractive intra-operative measurements can be performed using, for example, a wavefront aberrometer that measures refraction of the eye through the pupil. As described herein, keratometric data typically is taken with respect to the corneal apex, which does not necessarily coincide with the visual axis of the patient, resulting in different astigmatic measurements than those performed through the pupil. In addition, the intra-operative measurements of total refractive power are performed after the phaco incision has been made. Thus, these intra-operative measurements remove the guesswork involved in estimating the induced astigmatism that results from the phaco incision.

There are at least two advantages to deliberately misaligning the toric IOL prior to the intra-operative measurement of total refractive power of the eye, in some embodiments. First, if the toric IOL is initially misaligned by a sufficient angular amount in the counterclockwise direction (e.g., at least 15° in some embodiments, or at least 30° in other embodiments), then there is a low likelihood of having to make a, for example, counterclockwise rotation of the toric IOL after intra-operative measurements have been performed to determine the true axis of corneal astigmatism. This is beneficial because many toric IOLs are designed to only rotate easily in the clockwise direction. Of course, if a given toric IOL is designed to rotate easily in the counterclockwise direction, then the initial misalignment would be biased toward the clockwise direction.

In addition, the wavefront aberrometer described herein is capable of measuring the axis of astigmatism more accurately when an appreciable amount of astigmatism is present then in the case where very little astigmatism is present. Thus, within limits, the greater the magnitude of astigmatism present in the eye after the toric IOL is initially inserted in a misaligned state, the more accurately the wavefront aberrometer used to perform the intra-operative measurements of total refractive power of the eye can determine the axis of the astigmatism. If the toric IOL were initially misaligned by, for example, less than 15°, the magnitude of the residual astigmatism resulting from this misalignment may not be great enough in some cases to accurately measure the axis of that astigmatism. If, instead, the toric IOL is initially misaligned by greater than 15°, or by greater than 30°, then it is more likely that the axis of total refractive astigmatism can be accurately measured. This is important because the ultimate post-surgical residual astigmatism can only be reduced or minimized if the axis of corneal astigmatism can be accurately determined.

The amount of deliberate misalignment of the toric IOL performed at block 1708 of method 1700 is greater, possibly much greater, than any deliberate misalignment that a surgeon may employ in anticipation of inadvertent rotation of the toric IOL during aspiration of the visco-elastic material according to conventional techniques. In the case of the former, the amount of deliberate misalignment is intended to be large enough to avoid having to make a counterclockwise rotation of the toric IOL once the correct axis of the corneal astigmatism is known, whereas in the case of the latter it is assumed that the correct axis of the corneal astigmatism has been accurately estimated and the deliberate misalignment is only intended to compensate for any inadvertent rotation of the IOL which may occur during aspiration of the visco-elastic material from the capsular bag. In fact, in some embodiments, the latter technique of deliberately misaligning the toric IOL in anticipation of an inadvertent rotation during aspiration can be used in combination with the technique of block 1708.

As described herein, the techniques according to method 1700 allow the surgeon to initially insert the IOL at a somewhat arbitrary orientation rather than trying to accurately estimate the actual axis of corneal astigmatism (e.g., the surgeon does not necessarily have to attempt to correct the pre-operatively-measured keratometric astigmatic axis with an estimate of the induced astigmatism). Nor does the surgeon necessarily have to mark the position of the keratometric astigmatic axis pre-operatively while the patient is in an upright position. The toric IOL can be somewhat arbitrarily placed so long as this arbitrary orientation provides an adequate buffer against the possible need for counterclockwise rotations that may result from not previously having fully or partially considered or compensated for the following effects: the effect of induced astigmatism resulting from the phaco incision; the effect of cyclotorsion when the patient is moved to the supine position; and/or not having made an alignment mark on the limbus that corresponds to the estimated axis of corneal astigmatism, the alignment mark serving as a reference point from which to judge the amount of initial deliberate misalignment of the IOL.

Once the true magnitude and axis of corneal astigmatism have been determined (block 1712) based at least in part upon the intra-operatively measured total refractive power of the eye, the toric IOL can be rotated, at block 1714, from its deliberately misaligned state to proper alignment with the axis of the patient's corneal astigmatism. Once again, the amount and direction of necessary rotation of the toric IOL relative to the initial misaligned orientation can be determined by calculating the difference between the known misaligned axis of the toric IOL and the calculated axis of the patient's corneal cylinder, as indicated in the "Recommended Rotation" column of table 1600 in FIG. 16. This rotation value can be outputted to the surgeon, who can then use an instrument such as a Mendez gauge to make the proper amount of relative rotation. Once the toric IOL has been rotated to the correct axis of the patient's corneal astigmatism, the remainder of the cataract surgery can be performed conventionally. Another pseudophakic measurement can also be performed to check the accuracy of the alignment of the toric IOL.

In some embodiments, the necessary amount of rotation of the toric IOL from the misaligned state to one that is aligned with the calculated axis of corneal astigmatism is performed using a system that, for example, comprises a refractive measurement instrument that is mounted to and may be optically aligned with the surgical microscope being used to perform the cataract surgery. In some embodiments, the refractive measurement instrument is a wavefront aberrometer. Embodiments of a Talbot-Moiré wavefront aberrometer mounted to, and optically aligned with, the surgical microscope are described herein. The system for performing the necessary rotation of the toric IOL can also include an integrated module for providing an indicia to the surgeon of the axis to which the toric IOL should be aligned.

In some embodiments, this indicia is provided by any one of the optical angular measurement systems described herein. For example, the indicia can be provided by an optical system that projects a line or other alignment indicia onto the patient's eye that indicates the axis to which the toric IOL should be rotated, as described herein. For example, in some embodiments, a laser line is projected on the patient's eye that indicates this axis.

Figure 18:
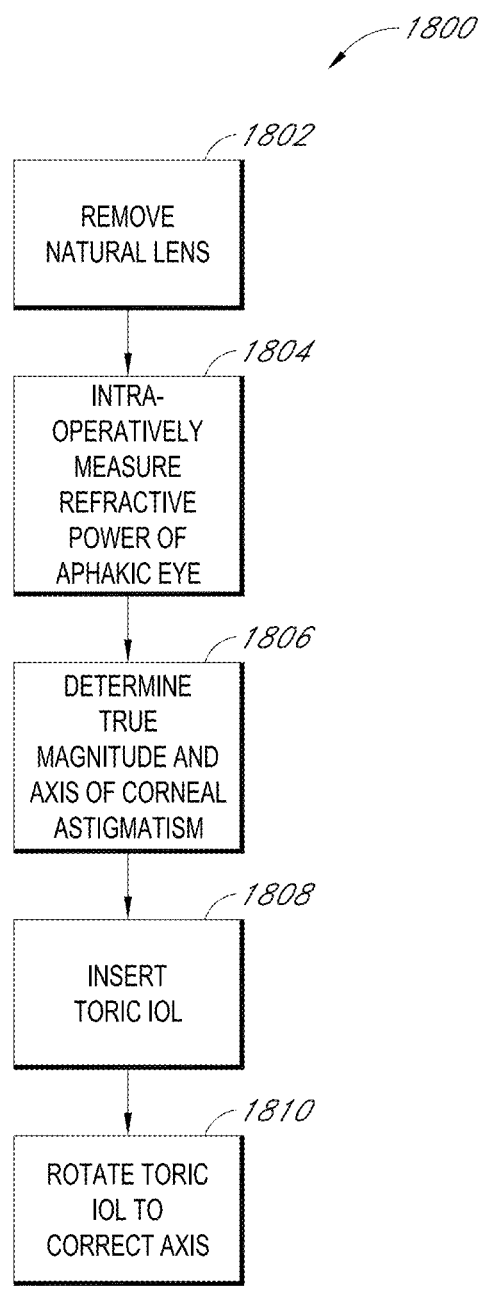
FIG. 18 is a flow chart illustrating a method for more accurately positioning a toric IOL during cataract surgery by intra-operatively measuring the refractive power of the aphakic eye.

FIG. 18 illustrates another embodiment where a method 1800 is used to accurately orient a toric IOL by intra-operatively measuring the refractive power of the aphakic eye. It should be understood by those of skill in the art that the aphakic and pseudophakic measurements described herein could be performed not only by a Talbot-Moiré wavefront aberrometer mounted to a surgical microscope, as described herein, but also by any other type of wavefront aberrometer, whether mounted to the surgical microscope or not. Other types of measurement devices, such as autorefractors, could also be used. In addition, handheld devices for measuring refractive power of the patient's eye can be used. The method 1800 begins at block 1802 where the surgeon removes the patient's natural lens through a phaco incision. Once the natural lens has been removed, at block 1804, the surgeon uses an ophthalmic instrument, for example as described herein, to perform an intra-operative measurement of the refractive power of the patient's aphakic eye. Since the patient's natural lens has already been removed at this point, the measured refractive power is attributable substantially only to the cornea. This measurement is taken through the pupil after the phaco incision has already been made. Thus, it does not suffer from the weaknesses of the pre-operative keratometric measurements described herein.

At block 1806, the magnitude and axis of astigmatism attributable to the cornea are determined using the aphakic intra-operative wavefront refractive measurements. A computer communicatively coupled to the instrument for performing this aphakic measurement can also be communicatively coupled with a database of available toric IOLs. After the aphakic measurement, this database can be electronically consulted to provide a recommendation to the surgeon of a suitable IOL to be used. At block 1808, the surgeon inserts the selected toric IOL. At block 1810, the surgeon rotates the toric IOL to align its axis with the axis of the patient's corneal astigmatism. Other aspects of the surgery can be performed conventionally.

In some embodiments, once the toric IOL has been inserted and rotationally oriented based upon the aphakic measurement of the refractive power of the patient's eye, an intraoperative pseudophakic measurement can be performed in order to determine the accuracy with which the toric IOL has been angularly aligned. For example, the total cylindrical power and axis of the patient's pseudophakic eye can be determined. The values of the cylindrical power and axis can then be used to determine whether the toric IOL is properly aligned. For example, if the toric IOL is theoretically fully-correcting and properly aligned, then the cylindrical power of the pseudophakic eye should be substantially 0.0 diopters. If the theoretically fully-correcting toric IOL results in an unexpected amount of residual astigmatism in the pseudophakic eye, then the crossed cylinder equations described herein can be used to back calculate the direction and amount by which the toric IOL should be rotated in order to achieve improved astigmatic correction.

For example, based on the inputs of the cylindrical power and axis of the aphakic eye, and on the cylindrical power and axis of the pseudophakic eye, the crossed cylinder equations can be used to determine the actual angular orientation of the toric IOL that was inserted into the eye (as well as confirming the astigmatic power of the toric IOL). These values can be used to determine whether residual astigmatism can be reduced by an adjustment to, for example, the angular orientation of the toric IOL (or possibly by substituting a toric IOL with a different amount of cylindrical power). For example, the direction and amount by which the toric IOL should be rotated to reduce residual astigmatism, if any, can be determined by calculating the difference between the calculated angular orientation of the toric IOL and the intended angular orientation that was determined based on the aphakic measurement. A computer can perform these calculations and output, for example, the direction and amount by which the toric IOL should be rotated.

If the toric IOL is non-fully-correcting, then the cylindrical power and axis values obtained from the pseudophakic measurement can be compared to the theoretically expected values of residual astigmatism, which can be obtained, for example, by using the crossed cylinder equations to determine the expected cylindrical power and axis resulting from the combination of the aphakic measurement of cylindrical power and axis with the known cylindrical power and intended axis of the toric IOL. If the measured cylindrical power and axis of the pseudophakic eye differs from the theoretically expected residual astigmatism values, then the pseudophakic measurements can be used to determine the direction and amount by which the toric IOL should be rotated in order to improve the residual astigmatism. For example, the crossed cylinder equations can be used to back calculate the direction and amount by which the toric IOL should be rotated, as described herein. These values can then be output to, for example, the surgeon. In this way, a pseudophakic measurement can be used to improve surgical outcomes even when an aphakic measurement is used to determine the angular axis to which a toric IOL should be aligned.

Figure 19:
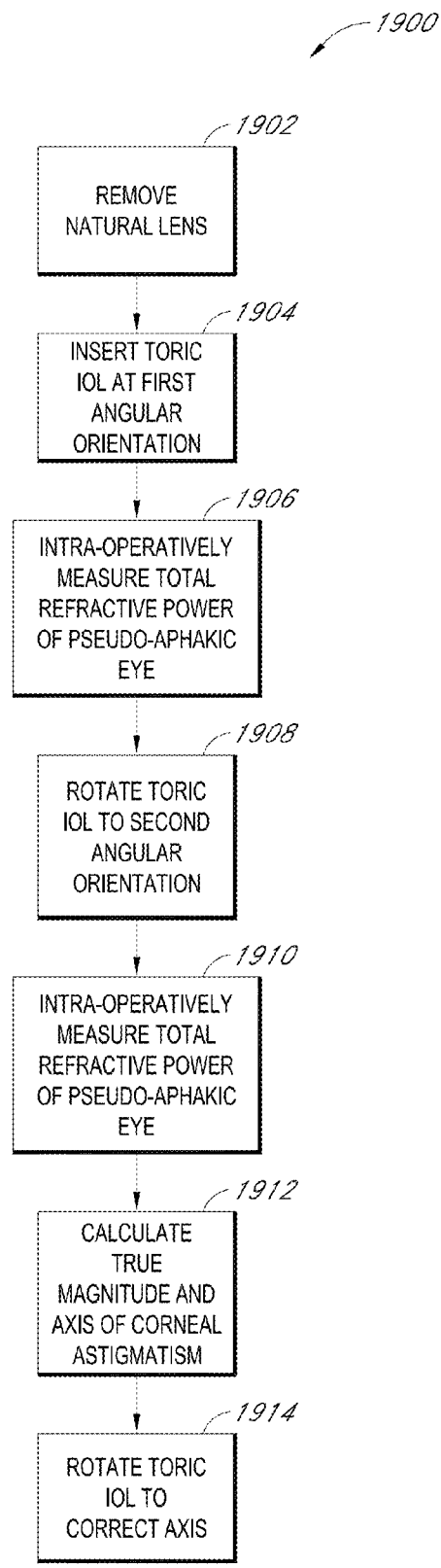
FIG. 19 is a flow chart illustrating a method for more accurately positioning a toric IOL during cataract surgery by performing at least two intra-operative refractive measurements of the pseudophakic eye while a toric IOL is positioned at two distinct angular orientations.

FIG. 19 illustrates another embodiment where a method 1900 is used to accurately orient a toric IOL by performing at least two intra-operative refractive measurements of the pseudophakic eye while a toric IOL is positioned at two distinct angular orientations. The method 1900 begins at block 1902 where the surgeon removes the patient's natural crystalline lens from the eye. In some embodiments, the surgeon may have already obtained an estimate of the axis of the patient's corneal astigmatism using, for example, keratometric data. Next, at block 1904, the surgeon inserts a toric IOL at a first angular orientation. The first angular orientation is arbitrary in some embodiments. However, in some embodiments, the first angular orientation is at least 15° from the estimated axis of the patient's corneal astigmatism. At block 1906, the surgeon intra-operatively measures the total refractive power of the patient's pseudophakic eye (the eye after the IOL has been implanted).

Next, the surgeon rotates the toric IOL to a second angular orientation (block 1908) distinct from the first. In some embodiments, the second angular orientation is separated from the first by an arbitrary, but known, amount. The amount and direction of angular separation between the first and second angular orientations can be measured using, for example, a Mendez gauge, or an angular measurement or tracking system integrated with the optical instrument for intra-operatively measuring the total refractive power of the patients pseudophakic eye, as described herein. Other methods and/or instruments for measuring the difference between the first and second angular orientations are also possible.

In some embodiments the second angular orientation is separated from the first by at least 15°. In some embodiments, the second angular orientation may also be separated from the estimated axis of corneal astigmatism by at least 15°. Once the toric IOL is positioned at the second angular orientation, at block 1910, the surgeon once again intra-operatively measures the total refractive power of the pseudophakic eye. The previously-described computer may be programmed with software that provides, for example, prompts or other information to help guide the surgeon through the process of determining when to perform a refractive power measurement, when, and by how much, to rotate the toric IOL from the first angular orientation to the second, etc.

Using the crossed cylinder equation and the measurements of the magnitude and axis of astigmatism of the pseudophakic eye at two distinct positions, a system of equations comprising two equations with two unknowns can be formed. For example, in some embodiments, the resulting mathematical relationship is a sine squared relationship. At block 1912, the system of equations can be solved to determine the magnitude and axis of corneal astigmatism which, when combined with the known magnitude and axis of the toric IOL at the two distinct positions, resulted in the measured total astigmatic refractive values of the patients pseudophakic eye at those two distinct positions. Finally, at block 1914, the surgeon can rotate the toric IOL to the correct axis which corresponds to the calculated astigmatic axis of the patient's cornea. The computer can calculate the amount and direction of this rotation, for example, by determining the difference between the second angular orientation of the toric IOL and the corneal astigmatic axis calculated from the system of equations.

It will be understood by those of skill in the art that, while certain procedures have been disclosed herein, these procedures can be altered and adapted, for example, depending upon the type of toric IOL used in a given cataract surgery, the available surgical equipment, the skill and customary techniques of the surgeon, the needs of the patient's, and other factors known to those of skill in the art. These alterations and adaptations can be made without departing from the scope of the invention. In addition, it should be appreciated that the steps of methods described herein can be reordered, and some steps may be omitted, in many instances.

The systems and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on computer-readable media (e.g., optical disks such as CDs or DVDs, hard disk drives, flash memories, diskettes, or the like) that, when read by a computer or other processing device, cause it to carry out the method.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, and/or elements may be altered, added, removed, or rearranged in ways that will be appreciated by those of ordinary skill in the art. While certain embodiments have been explicitly described, other embodiments will become apparent to those of ordinary skill in the art based on this disclosure.

What is claimed is:

1. An ophthalmic system, comprising:
   an optical refractive power measurement device, configured to be integrated with a surgical microscope, for intraoperatively measuring at least the cylindrical power and axis of a patient's eye, wherein the patient's eye is aphakic or pseudophakic; and
   an optical angular measurement device configured to be integrated with the surgical microscope or the optical refractive power measurement device, the optical angular measurement device being configured to provide at least one angular indicator for intraoperatively performing angular measurements or alignments with respect to the patient's eye,
   wherein the optical angular measurement device is configured to provide the at least one angular indicator with respect to measurement axes that are consistent with those of the optical refractive power measurement device.

2. The ophthalmic system of claim 1, wherein the angular indicia comprises a graphical pattern with angular graduation marks.

3. The ophthalmic system of claim 2, wherein the angular graduation marks are formed at intervals of at least every 5°.

4. The ophthalmic system of claim 1, wherein the at least one angular indicator comprises a movable indicator at a determined angular position for performing a surgical action.

5. The ophthalmic system of claim 1, wherein the at least one angular indicator comprises indicia of vertical and horizontal meridians, and wherein the optical refractive power measurement device and the optical angular measurement device are fixedly mounted such that the indicia of vertical and horizontal meridians are aligned with vertical and horizontal axes of the optical refractive power measurement device.

6. The ophthalmic system of claim 1, wherein the at least one angular indicator is projected onto the patient's eye.

7. The ophthalmic system of claim 1, wherein the at least one angular indicator is superimposed upon a view of the patient's eye.

8. An ophthalmic system, comprising:
   an optical refractive power measurement device, configured to be integrated with a surgical microscope, for intraoperatively measuring at least the cylindrical power and axis of a patient's eye; and
   an optical angular measurement device configured to be integrated with the surgical microscope or the optical refractive power measurement device, the optical angular measurement device being configured to provide at least one angular indicator for intraoperatively performing angular measurements or alignments with respect to the patient's eye,
   wherein the optical angular measurement device is configured to provide the at least one angular indicator with respect to measurement axes that are consistent with those of the optical refractive power measurement device,
   wherein the optical angular measurement device comprises:
   a reticle, the reticle comprising a plurality of angular graduation marks; and
   a light source for illuminating the reticle.

9. The ophthalmic system of claim 8, wherein the optical refractive power measurement device has a first optical pathway along a first optical axis, and the optical angular measurement device has a second optical pathway along a second optical axis, and wherein the surgical microscope is for viewing the patient's eye via a third optical pathway along a third optical axis during a surgical procedure, and further comprising a combining optical element for combining at least a portion of the second optical pathway with the third optical pathway.

10. The ophthalmic system of claim 9, wherein the second optical pathway and the third optical pathway are combined such that the at least one angular indicator is superimposed upon a view provided by the surgical microscope.

11. The ophthalmic system of claim 9, wherein the length of the second optical pathway from the reticle to the surgical microscope is substantially equal to the length of the third optical pathway from the surgical microscope to the patient's eye when the ophthalmic system is located at a predetermined working distance above the patient's eye.

12. The ophthalmic system of claim 9, wherein the reticle is located at substantially the same apparent distance from the surgical microscope as a patient's eye when the ophthalmic system is located at a predetermined working distance from the patient's eye.

13. The ophthalmic system of claim 9, wherein the reticle is located at an object plane of the surgical microscope.

14. The ophthalmic system of claim 9, wherein the optical refractive power measurement device comprises a separate housing having a fastener for removably attaching the optical refractive power measurement device to the surgical microscope, the housing having an optical pathway therethrough for passing visible light from the patient's eye to the surgical microscope, the combining optical element being located along the optical pathway.

15. The ophthalmic system of claim 9, wherein the combining optical element is configured such that the first and third optical axes are collinear along at least a portion thereof.

16. The ophthalmic system of claim 9, wherein the combining optical element is configured such that the second and third optical axes are collinear along at least a portion thereof.

17. The ophthalmic system of claim 9, wherein the combining optical element is configured such that the first and second optical axes are collinear along at least a portion thereof.

18. The ophthalmic system of claim 9, wherein the combining optical element is configured such that the first, second, and third optical axes are collinear along at least a portion thereof.

19. The ophthalmic systems of claim 9, wherein the optical refractive power measurement device and the optical angular measurement device are arranged with respect to one another such that the first and second optical axes are angularly separated but intersect at a predetermined working distance from the ophthalmic surgical device.

20. The ophthalmic system of claim 19, wherein the optical angular measurement device comprises a lens for imaging the reticle onto the patient's eye.

21. The ophthalmic system of claim 9, wherein the surgical microscope comprises a stereoscopic surgical microscope and has a support structure for movably supporting the surgical microscope over a supine patient.

22. The ophthalmic system of claim 9, wherein the at least one angular indicator is switchable between on and off states without disabling the view provided by the surgical microscope.

23. The ophthalmic system of claim 8, wherein the reticle comprises an opaque material and the angular graduation marks comprise optically transmissive regions formed in the opaque material.

24. The ophthalmic system of claim 8, wherein the reticle comprises a pattern of opaque regions surrounded by air or in optically transmissive material.

25. The ophthalmic system of claim 8, wherein the reticle comprises an alignment mark that is distinguished from the angular graduation marks.

26. The ophthalmic system of claim 24, wherein the alignment mark is rotatable.

27. The ophthalmic system of claim 8, wherein the optical refractive power measurement device comprises a wavefront aberrometer.

28. The ophthalmic system of claim 8, wherein the optical angular measurement device comprises a scanning light beam for creating the at least one angular indicator.

29. The ophthalmic system of claim 8, further comprising a computer configured to determine an angular alignment value based upon a measurement from the optical refractive power measurement device.

30. The ophthalmic system of claim 28, wherein the angular alignment value comprises the angular orientation to which a toric intraocular lens should be aligned based at least upon an aphakic or pseudophakic measurement of the patient's eye.

31. The ophthalmic system of claim 28, wherein the angular alignment value comprises the angular orientation at which an incision should be made in the patient's eye.

32. The ophthalmic system of claim 28, wherein the angular alignment value comprises the angular orientation to which a surgical implant should be aligned.

33. The ophthalmic system of claim 28, wherein the computer is configured to adjust the at least one angular indicator based on the angular alignment value.

34. The ophthalmic system of claim 8, wherein the optical angular measurement device comprises a computer controllable spatial light modulator.

35. The ophthalmic system of claim 8, wherein the optical angular measurement device comprises a holographic element for creating the at least one angular indicator.

36. The ophthalmic system of claim 8, wherein the optical angular measurement device comprises a spinning mirror for creating the at least one angular indicator.

37. The ophthalmic system of claim 8, wherein the optical angular measurement device comprises an acousto-optic modulator for creating the at least one angular indicator.

38. The ophthalmic system of claim 8, wherein the optical angular measurement device comprises an electro-optic modulator for creating the at least one angular indicator.

* * * * *